(12) United States Patent
Schindler et al.

(10) Patent No.: US 8,338,600 B2
(45) Date of Patent: Dec. 25, 2012

(54) COPPER-OXYGEN ADDUCT COMPLEXES, AND METHODS OF MAKING AND USE

(75) Inventors: Siegfried Schindler, Giessen (DE); Christian Würtele, Langgöns (DE)

(73) Assignee: Justus-Liebig-Universitat Giessen, Giessen (DE)

( * ) Notice: Subject to any disclaimer, the term of this patent is extended or adjusted under 35 U.S.C. 154(b) by 0 days.

(21) Appl. No.: 12/739,800

(22) PCT Filed: Oct. 27, 2008

(86) PCT No.: PCT/DE2008/001741
§ 371 (c)(1), (2), (4) Date: Apr. 27, 2010

(87) PCT Pub. No.: WO2009/052809
PCT Pub. Date: Apr. 30, 2009

(65) Prior Publication Data
US 2012/0016127 A1    Jan. 19, 2012

(30) Foreign Application Priority Data
Oct. 26, 2007    (DE) .......................... 10 2007 051 694

(51) Int. Cl.
*C07F 1/08*    (2006.01)
*B01J 27/24*    (2006.01)

(52) U.S. Cl. ............... 546/2; 502/200; 546/10; 548/101
(58) Field of Classification Search ................ 546/2, 10; 548/101; 502/200
See application file for complete search history.

(56) References Cited

U.S. PATENT DOCUMENTS
6,274,776 B1    8/2001    Henrick et al.

FOREIGN PATENT DOCUMENTS
DE    600 24 605 T2    8/2006

OTHER PUBLICATIONS

A. Blackman, "The coordination chemistry of tripodal tetraamine ligands", Polyhedron 24 (2005) 1-39.
K. Komiyama et al, "Dioxygen Reactivity of Copper(I) Complexes with Tetradentate Tripodal Ligands Having Aliphatic Nitrogen Donors: Synthesis, Structures, and Properties of Peroxo and Superoxo Complexes", Bull. Chem. Soc. Jpn., 77, 59-72 (2004).
C. Kato et al., "Oxidation catalysis of microporous metal carboxylate complexes", ScienceDirect, C.R. Chimie 10 (2007) 284-294.
M. Weitzer et al., "Reversible Binding of Dioxygen by the Copper(I) Complex with Tris(2-dimethylaminoethyl)amine ($Me_6$tren) Ligand", Inorg. Chem. 2003, 42, 1800-1806.
R. Jacobson et al., "A $Cue_2$-$O_2$ Complex. Crystal Structure and Characterization of a Reversible Dioxygen Binding System", J. Am. Chem. Soc. 1988, 110, 3690-3692.
M. Schatz et al., "Syntheses and characterization of copper complexes of the ligand (2-aminoethyl)bis(2-pyridylmethyl)amine (unspenp) and derivatives", Dalton Trans. 2003, 1480-1487.
S. Schindler, "Reactivity of Copper(I) Complexes Towards Dioxygen", Eur. J. Inorg. Chem. 2000, 2311-2326.
M. Weitzer et al., "Low temperature stopped-flow studies in inorganic chemistry", J. Chem. Soc., Dalton Trans., 2002, 686-694.
M. Becker et al., "Reversible Binding of Dioxygen by a Copper(I) Complex with Tris(2-dimethylaminoethyl)amine ($Me_6$tren) as a Ligand", Chem. Eur. J. 1999, 5 No. 11, 3124-3129.
G. Britovsek et al., "Non-heme Iron(II) Complexes Containing Tripodal Tetradentate Nitrogen Ligands and Their Application in Alkane Oxidation Catalysis", Inorganic Chemistry, vol. 44, No. 22, 2005, 8125-8134.

*Primary Examiner* — Charanjit Aulakh
(74) *Attorney, Agent, or Firm* — Clark & Brody

(57) ABSTRACT

The invention at hand describes Cu-(II)-oxygen adduct complexes, which are stable at room temperature, as well as methods for their production. In this, compounds of the general formula $[L\text{-}Cu\text{—}O\text{—}O\text{—}Cu\text{-}L](BAr_4)_2$ are concerned. Here, $BAr_4^-$ is a tetraarylborate anion, selected from tetraphenylborate and tetrakis(3,5-trifluoromethyl)phenylborate. L represents a tripodal tetradentate ligand, wherein, each of the four binding sites of the tripodal tetradentate ligand is a nitrogen atom. Each of the three podal ligands is suitable for comprising an aliphatic amine or a nitrogen-containing heteroaromatic compound independently of one another. A bridge of one to four carbon atoms is located between the central nitrogen atom and the nitrogen atom of each of the podal ligands.

The Cu-(II)-oxygen adduct complexes according to the present invention are produced, by initially reacting the ligand L with a Cu-(I) salt to [Cu-L]X. Subsequently, the anion X of the Cu-(I) complex [Cu-L]X is replaced with tetraarylborate and the compound $[Cu\text{-}L]BAr_4$ obtained in this way is finally exposed to an oxygen-containing atmosphere. Hereby, $[L\text{-}Cu\text{—}O\text{—}O\text{—}Cu\text{-}L](BAr_4)_2$ is formed.
The Cu-(II)-oxygen adduct complexes are suitable for being used as oxidation catalysts, for example for the oxidation of benzene to phenol or methane to methanol, for the oxidation of hydrogen, aromatic and aliphatic, saturated and unsaturated hydrocarbons, as well as alcohols and amines.
Furthermore, detection of the Cu-(II)-oxygen adduct complexes according to the present invention is suitable for being used for the detection of oxygen.

17 Claims, 12 Drawing Sheets

COPPER-OXYGEN ADDUCT COMPLEXES, AND METHODS OF MAKING AND USE

The invention at hand describes novel copper-(II)-oxygen adduct complexes of the general type [L-Cu—O—O—Cu-L](BAr$_4$)$_2$, as well as methods for their production. In this, L is a tetradentate tripodal ligand, whose four binding sites are represented through nitrogen atoms. BAr4- is a tetraarylborate anion. The complexes according to the present invention are, in contrast to previously known Cu-(II)-oxygen adduct complexes, stable at room temperature. The Cu-(II)-oxygen adduct complexes according to the present invention are suitable for being used as oxidation catalysts.

DESCRIPTION AND INTRODUCTION OF THE GENERAL AREA OF THE INVENTION

The invention at hand concerns the areas of inorganic chemistry/complex chemistry, organic chemistry and redox chemistry.

STATE OF THE ART

Oxidation reactions play a large role in technical chemistry. The oxidation of benzene to phenol and the oxidation of methane to methanol are given as examples.

In many cases, atmospheric oxygen is not suitable for being directly used, and suitable oxidizing agents must first be produced.

It has been assumed for some time that copper-oxygen adduct complexes would be able to represent suitable oxidizing agents and catalysts, respectively, for numerous industrial oxidations, for example, the oxidation of hydrogen, aromatic and aliphatic hydrocarbons, as well as alcohols and amines.

With many of the previously known copper-oxygen adduct complexes, the copper atom is coordinated through tripodal tetradentate, nitrogen-containing ligands. Frequently used ligands are, for example,

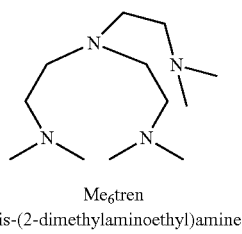

Me$_6$tren
tris-(2-dimethylaminoethyl)amine

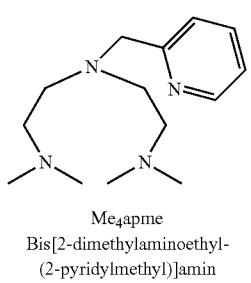

Me$_4$apme
Bis[2-dimethylaminoethyl-(2-pyridylmethyl)]amin

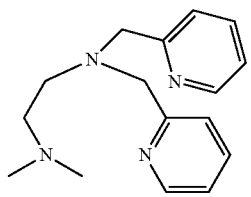

Me$_4$uns-penp
(2-dimethylaminoethyl)-bis(2-pyridylmethyl)amine

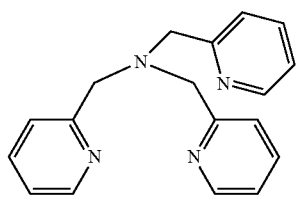

tmpa
tris-[(2-pyridyl)-methyl]amine

The named copper-oxygen adduct complexes, the tetradentate, tripodal, nitrogen-containing ligands, and the corresponding complexes of the two-valued iron, respectively, are described, for example, in 1. R J Jacobson et al.: "A Cu$_2$—O$_2$ Complex. Crystal Structure and Characterization of a Reversible Dioxygen Binding System." J Am Chem Soc 1988, 110, 3690-3692
2. M Becker et al.: "Reversible Binding of Dioxygen by a Copper(I) Complex with Tris(2-dimethylaminoethyl)amine (Me$_6$tren) as a Ligand." Chem Eur J 1999, 5, 3124-3128
3. S Schindler: "Reactivity of Copper(I) Complexes Towards Dioxygen." Eur J Inorg Chem 2000, 2311-2326
4. M Weitzer et al.: "Low temperature stopped-flow studies in inorganic chemistry." J Chem Soc, Dalton Trans, 2002, 686-694
5. M Schatz et al.: "Syntheses and characterization of copper complexes of the ligand (2-aminoethyl)bis(2-pyridylmethyl)amine (uns-penp) and derivatives." Dalton Trans, 2003, 1480-1487
6. M Weitzer et al.: "Reversible Binding of Dioxygen by the Copper(I) Complex with Tris(2-dimethylaminoethyl)amine (Me$_6$tren) Ligand." Inorg Chem 2003, 42, 1800-1806
7. K Komiyama et al.: "Dioxygen Reactivity of Copper(I) Complexes with Tetradentate Tripodal Ligands Having Aliphatic Nitrogen Donors: Synthesis, Structures, and Properties of Peroxo and Superoxo Complexes." Bull Chem Soc Jpn, 2004, 77, 59-72
8. A G Blackmann: "The coordination chemistry of tripodal tetraamine." Polyhedron 2005, 24, 1-39
9. G J P Britovsek et al.: "Non-heme Iron(II) Complexes Containing Tripodal Tetradentate Nitrogen Ligands and Their Application in Alkane Oxidation Catalysis." Inorg Chem 2005, 44, 8125-8134

All of the Cu-(I)- and Cu-(II)-oxygen adduct complexes previously known are thermally instable; almost all are stable for a short time only at temperatures considerably below 0° C. Due to this instability, they are less suitable as oxidizing agents or catalysts for the oxidation of substrates.

The state of the art, however, comprises metal-oxygen compounds which are applied as catalysts for oxidation reactions.

Thus, U.S. Pat. No. 6,274,776 B1 describes a method for the production of 2,5-dichlorophenol through selective oxidation of 1,4-dichlorobenzene using peroxo-, hydroperoxo-, superoxo- or alkylperoxo-metal compounds as catalysts. In this, all the main group metals, with the exception of the alkali and alkaline earth metals, as well as transition or rare earth metals, come into consideration. However, the oxidation reaction described runs only in the presence of acids, and the catalysts do not comprise any tripodal tetradentate ligands.

DE 600 24 605 T2 describes methods for the controlled radical polymerization of (meth)acrylamides with the use of a catalyst. The catalyst comprises a transition metal salt—for example, a copper halide—, a tripodal tetradentate, nitrogen-containing compound, which complexes the transition metal salt, as well as a counterion. The tripodal tetradentate, nitrogen-containing compound is suitable for comprising, for example, Me$_6$tren, tmpa or bis(2-pyridylmethyl)-(2-phenolylmethyl)amine. The counterion is preferably a complex onium-based anion, however, does not comprise in any case boron as the central atom. Complexes, which comprise the functional unit [~Cu—O—O—Cu~], are likewise not disclosed in DE 600 24 605 T2.

The invention at hand overcomes the disadvantages in the state of the art, providing novel Cu-(II)-oxygen adduct complexes, which are thermally stable, i.e. are suitable for being stored as a solid without decomposing at room temperature and, furthermore, in an oxygen-containing atmosphere.

Aim

The aim of the invention at hand is to provide novel copper-(II)-oxygen adduct complexes, which are stable at room temperature, as well as methods for their production.

Achievement of the Aim

The aim of providing novel copper-(II)-oxygen adduct complexes is achieved according to the present invention through compounds of the general formula

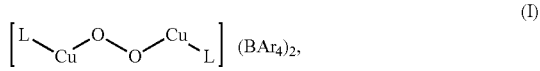

(I)

wherein
BAr$_4$ stands for a tetraarylborate anion, selected from tetraphenylborate and tetrakis(3,5-trifluoromethyl)phenylborate and
L represents a tripodal tetradentate ligand, wherein
a) each of the four binding sites of the tripodal tetradentate ligand is a nitrogen atom, and
b) three podal, nitrogen-containing ligands are bound to the central nitrogen atom, and
c) each of the three podal, nitrogen-containing ligands comprises an aliphatic amine or a nitrogen-containing heteroaromatic compound independently of one another, and
d) a bridge of one to four carbon atoms is located between the central nitrogen atom and the nitrogen atom of each of the podal ligands,
e) the bridge of one to four carbon atoms exclusively comprises sp$^3$-hybridized, aliphatic carbon atoms, if the podal ligand is an aliphatic amine, or
f) if the podal ligand is a nitrogen-containing heteroaromatic compound, the bridge of one to four carbon atoms comprises exactly one sp$^2$-hybridized carbon atom, wherein this sp$^2$-hybridized carbon atom is part of the heterocyclical aromatic compound and is located in the 2-position to at least one nitrogen atom of the heterocyclic ring.

Surprisingly, it was found that the copper-(II)-oxygen adduct complexes according to the present invention are thermally stable, in contrast to the previously known Cu-(II)-oxygen adduct complexes. It is decisive for the thermal stability of the Cu-(II)-complex according to the present invention that a tetraarylborate is selected as the anion, since the corresponding Cu-(II)-oxygen adduct complexes are thermally instable with other anions (for example perchlorate).

Tetraarylborate anions BAr$_4^-$ according to the present invention are tetraphenylborate and tetrakis(3,5-trifluoromethyl)phenylborate (BARF).

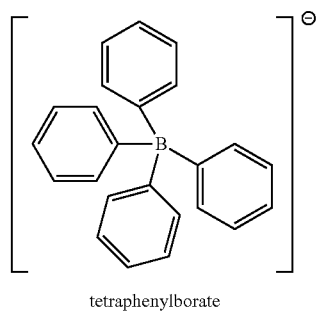

tetraphenylborate

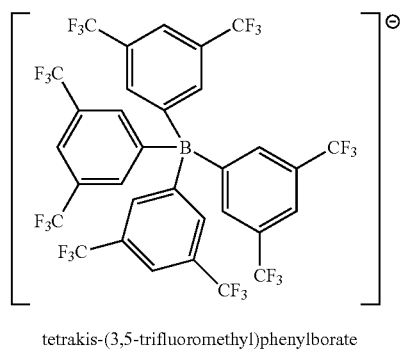

tetrakis-(3,5-trifluoromethyl)phenylborate

Here, "thermally stable" is understood to mean that the Cu-(II)-oxygen adduct complexes according to the present invention are stable as a solid at room temperature and in an oxygen-containing atmosphere.

In the complexes according to the present invention, each of the two Cu atoms is coordinated by a tripodal tetradentate ligand. This tripodal tetradentate ligand L, is a ligand of the general formula

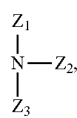

(II)

wherein $Z_1$, $Z_2$ and $Z_3$ are selected independently of one another from
an aliphatic amine, which is bound to an alkylene group of one to four carbon atoms, according to the formula

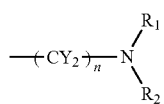

(III)

and a nitrogen-containing heteroaromatic compound, which is bound in the 2-position to at least one of its nitrogen atoms to an alkylene group of zero to three carbon atoms, according to

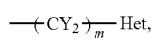

(IV)

so that the aromatic sp²-hybridized carbon atom, which is located in the 2-position to at least one nitrogen atom of the heteroaromatic compound, forms, together with the alkylene group —(CY$_2$)$_m$—, a bridge of one to four carbon atoms between the central nitrogen atom of the ligand L and the at least one nitrogen atom of the heteroaromatic compound, wherein Y, n, m, R$_1$, R$_2$ and Het have the following meanings and, for each of the groups Z$_1$, Z$_2$ and Z$_3$ are suitable for being selected independently of one another:

Y=H or F, n=1, 2, 3, 4, m=0, 1, 2, 3, and R$_1$ and R$_2$ are selected independently of one another from

—H, —CH$_3$, —CH$_2$CH$_3$, —CH$_2$CH$_2$CH$_3$, —CH(CH$_3$)$_2$, C(CH$_3$)$_3$,

—CF$_3$, —CF$_2$CF$_3$, —CF$_2$CF$_2$CF$_3$, —CF(CF$_3$)$_2$, C(CF$_3$)$_3$, wherein, for the case where one of the two groups R$_1$ or R$_2$ represents —C(CH$_3$)$_3$ or —C(CF$_3$)$_3$, the other group R$_1$ or R$_2$ is selected from —H, —CH$_3$ and CF$_3$ phenyl, pentafluorophenyl, methylphenyl, dimethylphenyl, trifluoromethylphenyl, (bis-trifluoromethyl)phenyl, and Het is a nitrogen-containing heteroaromatic, selected from

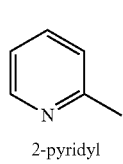
2-pyridyl

3,4,5,6-tetrafluoro-2-pyridyl

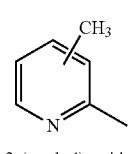
2-(methyl)pyridyl

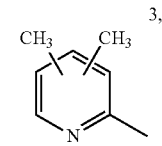
2-(dimethyl)pyridyl 2-(trifluoromethyl)pyridyl

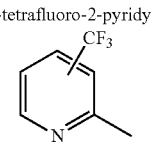
2-(di-trifluoromethyl)pyridyl 2-pyrryl

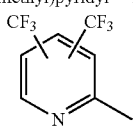

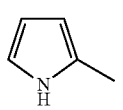

-continued

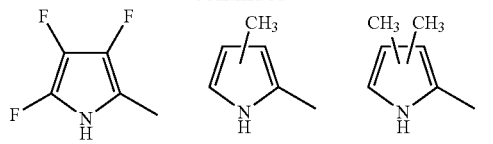
3,4,5-trifluoro-2-pyrryl  2-(methyl)pyrryl  2-(dimethyl)pyrryl

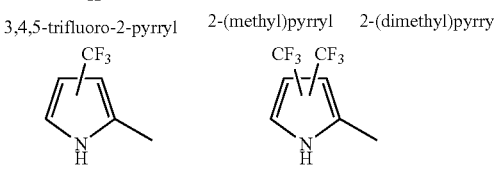
2-(trifluoromethyl)pyrryl  2-(di-trifluoromethyl)pyrryl

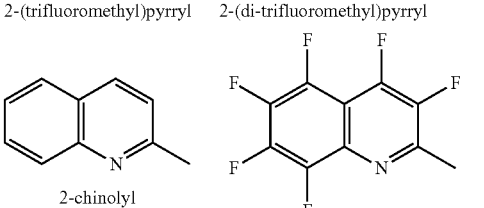
2-chinolyl  3,4,5,6,7,8-hexafluoro-2-chinolyl

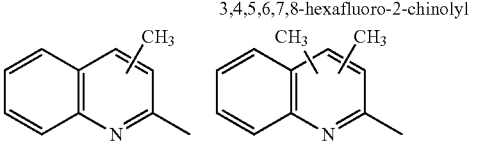
2-(methyl)chinolyl  2-(dimethyl)chinolyl

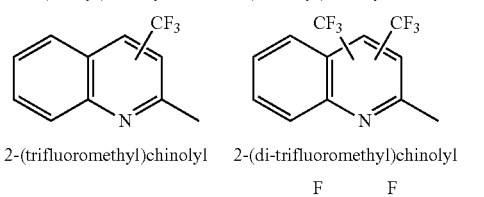
2-(trifluoromethyl)chinolyl  2-(di-trifluoromethyl)chinolyl

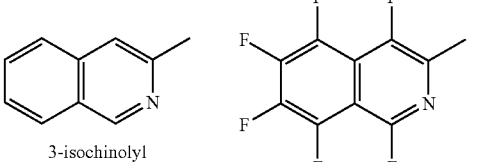
3-isochinolyl  1,4,5,6,7,8-hexafluoro-3-isochinolyl

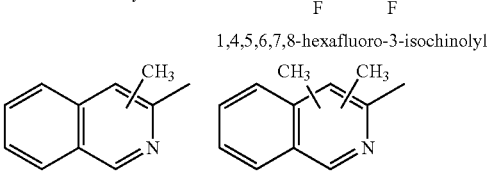
3-(methyl)isochinolyl  3-(dimethyl)isochinolyl

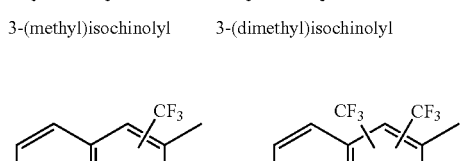
3-(trifluoromethyl)isochinolyl  3-(di-trifluoromethyl)isochinolyl

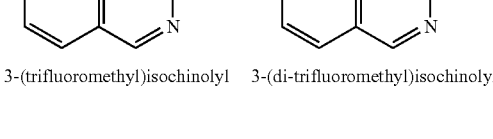
3-pyrazyl  4,5-difluoro-3-pyrazyl  3-(methyl)pyrazyl

-continued

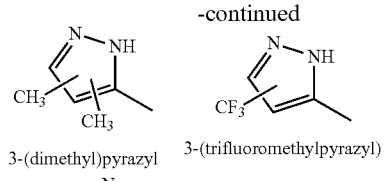
3-(dimethyl)pyrazyl    3-(trifluoromethylpyrazyl)

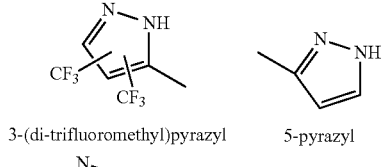
3-(di-trifluoromethyl)pyrazyl    5-pyrazyl

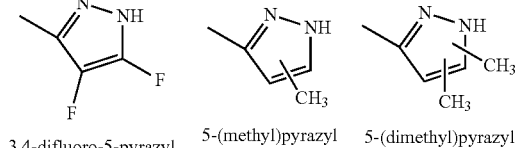
3,4-difluoro-5-pyrazyl    5-(methyl)pyrazyl    5-(dimethyl)pyrazyl

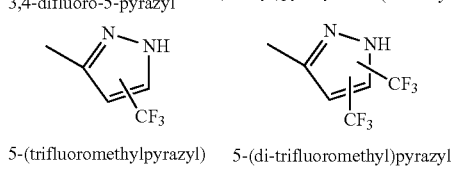
5-(trifluoromethylpyrazyl)    5-(di-trifluoromethyl)pyrazyl

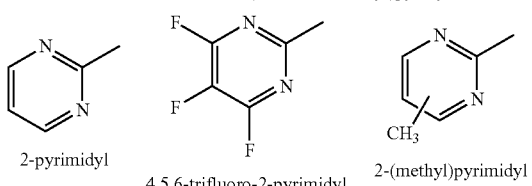
2-pyrimidyl    4,5,6-trifluoro-2-pyrimidyl    2-(methyl)pyrimidyl

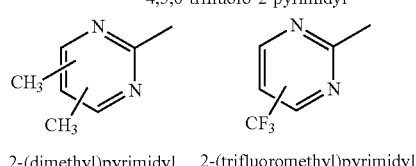
2-(dimethyl)pyrimidyl    2-(trifluoromethyl)pyrimidyl

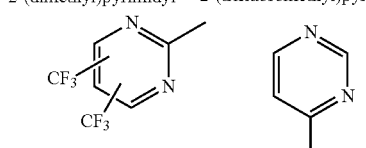
2-(di-trifluoromethyl)pyrimidyl    4-pyrimidyl

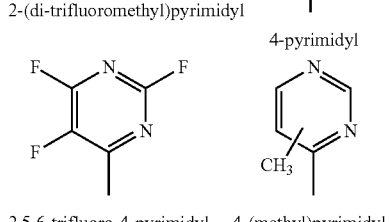
2,5,6-trifluoro-4-pyrimidyl    4-(methyl)pyrimidyl

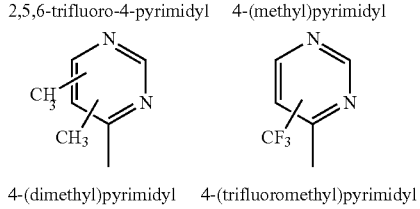
4-(dimethyl)pyrimidyl    4-(trifluoromethyl)pyrimidyl

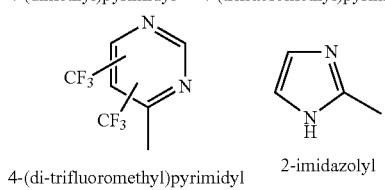
4-(di-trifluoromethyl)pyrimidyl    2-imidazolyl

-continued

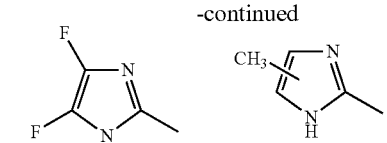
4,5-difluoro-2-imidazolyl    2-(methyl)imidazolyl

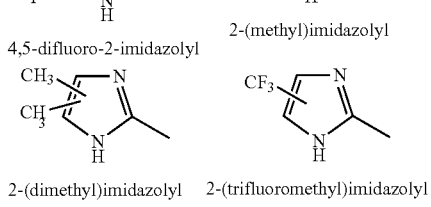
2-(dimethyl)imidazolyl    2-(trifluoromethyl)imidazolyl

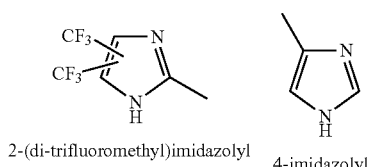
2-(di-trifluoromethyl)imidazolyl    4-imidazolyl

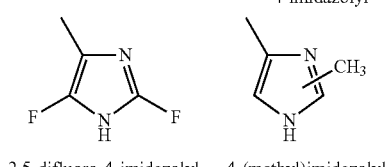
2,5-difluoro-4-imidazolyl    4-(methyl)imidazolyl

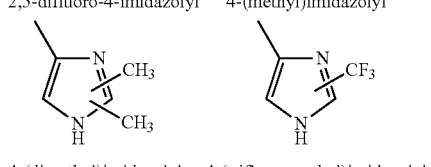
4-(dimethyl)imidazolyl    4-(trifluoromethyl)imidazolyl

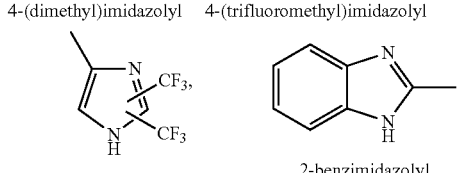
4-(di-trifluoromethyl)imidazolyl    2-benzimidazolyl

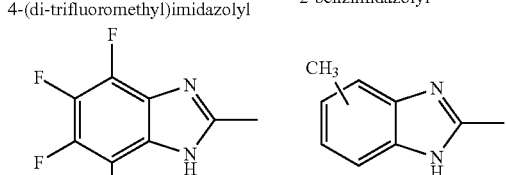
4,5,6,7-tetrafluoro-2-benzimidazolyl    2-(methyl)benzimidazolyl

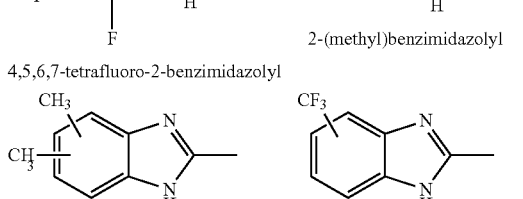
2-(dimethyl)benzimidazolyl    2-(trifluoromethyl)benzimidazolyl

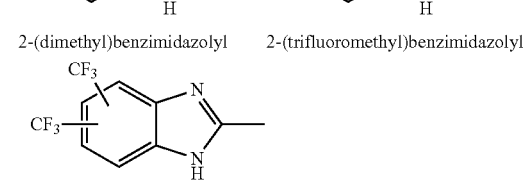
2-(di-trifluoromethyl)benzimidazolyl

If $Z_1$, $Z_2$ and/or $Z_3$ is a group according to formula III, then —(CY$_2$)$_n$— represents the bridge of one to four carbon atoms, which is located, according to the present invention, between the central nitrogen atom and the nitrogen atom of the respective podal ligand.

If $Z_1$, $Z_2$ and/or $Z_3$ is a group according to the formula IV, then —$(CY_2)_m$— represents, together with the sp$^2$-hybridized carbon atom of the heteroaromatic ring, which is located in the 2-position to at least one nitrogen atom, the bridge of one to four carbon atoms, which is located, according to the present invention, between the central nitrogen atom and the nitrogen atom of the respective podal ligand.

Within the framework of the invention at hand, the term "ligand" refers to a tripodal tetradentate ligand, wherein each of its four binding sites is a nitrogen atom. In this, three nitrogen-containing ligands are bound at the central nitrogen atom. The three nitrogen-containing ligands, which are bound to the central nitrogen atom, are called "podal ligands".

With the aforementioned formula II and the following formulas III, IV, V, VI, VII and VIII derived therefrom, $NZ_1Z_2Z_3$ is the "ligand" according to this, while $Z_1$, $Z_2$ and $Z_3$ represent the three "podal ligands".

In a preferred embodiment, the podal ligands $Z_1$, $Z_2$ and $Z_3$ are selected independently of one another from an aliphatic amine, which is bound to an alkylene group of one to four carbon atoms, according to the formula

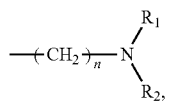

(V)

and a nitrogen-containing heteroaromatic compound, which is bound in the 2-position to at least one of its nitrogen atoms to an alkylene group of zero to three carbon atoms, according to the formula

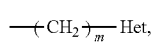

(VI)

wherein n, m, $R_1$, $R_2$ and Het are suitable for being selected independently of one another for each of the groups $Z_1$, $Z_2$ and $Z_3$ and for having the aforementioned meanings. In the case that one of the two groups $R_1$ or $R_2$ represents —$C(CH_3)_3$ or —$C(CF_3)_3$, the other group $R_1$ or $R_2$ is selected from —H, —$CH_3$ and $CF_3$ in this embodiment as well. This embodiment concerns podal ligands, in which the alkylene groups, located between the central nitrogen atom and the podal ligands, are not fluorinated.

In a further embodiment, those podal ligands $Z_1$, $Z_2$ and $Z_3$, in which the bridge of carbon atoms, which is located between the central nitrogen atom and the nitrogen atom of each podal ligand, comprises exactly two carbon atoms, are preferable, wherein these bridge carbon atoms are not fluorinated. If one of this type of podal ligands is an aliphatic amine, then it is an amine according to the formula

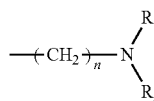

(VII)

If one of this type of podal ligands comprises, in contrast, a nitrogen-containing heteroaromatic compound, which is bound in the 2-position to at least one of its nitrogen atoms to an alkylene group, then the alkylene group represents a methylene group in this case. The podal ligand comprising a nitrogen-containing heteroaromatic compound is described, in this case, through the formula $CH_2$—Het (VIII), Hereby, $R_1$ and $R_2$ in formula (VII), as well as Het in formula (VIII), have the aforementioned meanings. $R_1$, $R_2$ and Het are suitable for being selected independently of one another for each of the groups $Z_1$, $Z_2$ and $Z_3$, wherein, in the case that one of the two groups $R_1$ or $R_2$ represents —$C(CH_3)_3$ or —$C(CF_3)_3$, the other group $R_1$ or $R_2$ is selected from —H, —$CH_3$ and $CF_3$.

Very particularly preferable are ligands L,
in which the bridges between the central nitrogen atom and the nitrogen atom of each of the podal ligands comprise exactly two carbon atoms, and
in which the carbon atoms are not fluorinated,
wherein $R_1$ and $R_2$ are selected independently of one another, as well as independently of each podal ligand, from
—H, —$CH_3$, —$CH_2CH_3$, —$CH_2CH_2CH_3$, —$CH(CH_3)_2$, $C(CH_3)_3$,
wherein, in the case, that one of the two groups $R_1$ or $R_2$ represents —$C(CH_3)_3$, the other group $R_1$ or $R_2$ is selected from —H and —$CH_3$.
and
Het is selected from
2-pyridyl, 2-pyrryl, 2-chinolyl, 3-isochinolyl, 3-pyrazyl, 5-pyrazyl, 2-pyrimidyl, 4-pyrimidyl, 2-imidazolyl, 4-imidazolyl, 2-benzimidazolyl.

The most preferable are those copper-(II)-oxygen adduct complexes of the general formula [L-Cu—O—O—Cu-L] $(BAr_4)_2$, in which the tripodal tetradentate ligand L is selected from tris-(2-dimethylaminoethyl)-amine, bis-[2-dimethylaminoethyl-(2-pyridylmethyl)]-amine, [(2-dimethylaminoethyl)-bis-(2-pyridylmethyl)]-amine, tris-[(2-pyridyl)-methyl]-amine.

With all of the embodiments mentioned, those adduct complexes in which the anion is tetraphenylborate are preferable.

The aim of providing a method for the production of the copper-(II)-oxygen adduct complexes according to the present invention is achieved, according to the present invention, with a method comprising the steps
a) complexing the ligand L with a Cu-(I)-compound [Cu $(R_3)_4$]X in a polar aprotic solvent under inert gas atmosphere,
b) replacement of the anion X of the Cu-(I)-complex [Cu-L]X with tetraarylborate in a polar aprotic solvent under inert gas atmosphere,
c) bringing the [Cu-L]-tetraarylborate obtained after carrying out step b) into contact with an oxygen-containing atmosphere,
d) isolation and drying of the complex [L-Cu—O—O—Cu-L]$(BAr_4)_2$ obtained after carrying out step c).

The production of the Cu-(II)-oxygen adduct complexes according to the present invention occurs according to the general reaction scheme L+[Cu(R$_3$)$_4$]X→[Cu-L]X  a)

[Cu-L]X+MeBAr$_4$→[Cu-L]BAr$_4$  b)

2[Cu-L]BAr$_4$+O$_2$→[L-Cu—O—O—Cu-L](BAr$_4$)$_2$  c)

Hereby, L is a ligand according to the definition above.

In the first step, the ligand L is reacted in a polar aprotic solvent with a salt [Cu(R$_3$)$_4$]X under inert gas atmosphere to the corresponding [Cu-(I)-L] complex.

$R_3$ is able to be acetonitrile or no atom.

If R$_3$ is acetonitrile, then the anion X is selected from hexafluorophosphate PF$_6^-$, tetrafluoroborate BF$_4^-$, perchlorate ClO$_4^-$, hexafluoroantimonate SbF$_6^-$, triflate SO$_3$CF$_3^-$ and tetraphenylborate BPh$_4^-$, tetrakis(3,5-trifluoromethyl)phenylborate, wherein PF$_6^-$, BF$_4^-$ and ClO$_4^-$ are preferable.

If R$_3$ is no atom, then X is selected from chloride Cl$^-$, bromide Br$^-$ and iodide I$^-$. The polar aprotic solvent is preferably acetone, acetonitrile or propionitrile. Preferably, the ligand L and [Cu(R$_3$)$_4$]X are used in a molar ratio of approx. 1:1, wherein the ligand is able to be present in a molar excess of up to 10%.

In the second step, the solution of the complex [L-Cu(I)]X obtained in step a) is reacted with a solution of a metal tetraarylborate under inert gas atmosphere.

The metal tetraphenylborate is preferably an alkali metal tetraarylborate, for example, sodium-tetraarylborate or potassium-tetraarylborate.

A polar aprotic solvent, for example acetone, acetonitrile, or propionitrile, serves as the solvent for the metal tetraarylborate. Advantageously, the same polar aprotic solvent is selected in step b) as in step a).

The molar ratio of [L-Cu(I)]X to tetraarylborate advantageously comprises approx. 1:1, wherein tetraarylborate is able to be present in a light excess of up to 10%. The reaction of the ligand L with [Cu(R$_3$)$_4$]X, as well as its subsequent reaction with tetraarylborate to [L-Cu]BAr$_4$, are carried out under inert gas atmosphere. An inert gas atmosphere is understood to be an oxygen-free inert gas atmosphere. Preferably, this inert gas atmosphere comprises argon, helium or nitrogen.

The solution of the [L-Cu-(I)]BAr$_4$ complex obtained in step b) is subsequently exposed to an oxygen-containing atmosphere according to step c). In this, the corresponding Cu-(II)-peroxo adduct complex [L-Cu—O—O—Cu-L](BAr$_4$)$_2$ is formed.

Under "exposing to an oxygen-containing atmosphere", it is understood that [L-Cu-(I)]BAr$_4$ is exposed to air, oxygen gas or an oxygen-air mixture. The [L-Cu-(I)]BAr$_4$ solution is cooled to temperatures <−70° C., before it is exposed to the oxygen-containing atmosphere.

The Cu-(II)-peroxo adduct complex [L-Cu—O—O—Cu-L](BAr$_4$)$_2$ formed is subsequently precipitated through the addition of an aprotic solvent, filtered and dried. Precipitation occurs in this at deep temperatures <−70° C., and drying occurs in the oxygen flow.

Aprotic solvents suitable for precipitation are known to persons skilled in the art and are suitable for being used without leaving the scope of protection of the patent claims. For example, diethylether, pentane, hexane, heptane and cycloalkanes with 5 to 8 carbon atoms are suitable.

Alternatively, the product from step b), namely [L-Cu-(I)]BAr$_4$, is already suitable for being isolated from the solvent and dried. This occurs, for example, through precipitation with an aprotic solvent, filtration of the solid and its drying under inert gas atmosphere in vacuum. Diethylether, pentane, hexane, heptane and cycloalkanes with 5 to 8 carbon atoms, for example, are suitable as an aprotic solvent.

If [L-Cu-(I)]BAr$_4$ is already isolated and dried as a solid, then it is suitable for being exposed to an oxygen-containing atmosphere as described above in step c), wherein the Cu-(II)-peroxo adduct complex [L-Cu—O—O—Cu-L](BAr$_4$)$_2$ is formed. Isolation of the solid [L-Cu-(I)]BAr$_4$ is able to occur at room temperature, wherein drying occurs, however, under inert gas atmosphere. Subsequently, [L-Cu-(I)]BAr$_4$ is exposed to an oxygen-containing atmosphere as a solid at room temperature, wherein [L-Cu—O—O—Cu-L](BAr$_4$)$_2$ is formed.

The Cu-(II)-oxygen adduct complexes are suitable for being used as oxidation catalysts, for example for the oxidation of benzene to phenol or methane to methanol, for the oxidation of hydrogen, aromatic and aliphatic, saturated and unsaturated hydrocarbons, as well as alcohols and amines.

Furthermore, detection of the Cu-(II)-oxygen adduct complexes is suitable for being used for the detection of oxygen. For that purpose, a complex [L-Cu(I)]BAr$_4$] is provided in a device, which is able to be sealed off from the outer atmosphere with the help of one or several stopcocks. This device is, for example, a flow line or a glass container. By opening one or more of the stopcocks of the device, the gas mixture to be examined is brought into contact with the complex according to the present invention. Without the presence of oxygen, the complex keeps its white or yellow color, respectively, whereas it becomes deep blue in the presence of oxygen, since [L-Cu—O—O—Cu-L](BAr$_4$)$_2$ forms.

The Cu-(II)-oxygen adduct complexes according to the present invention are suitable for being deposited optionally as reactive components in mesoporous phases such as molecular sieves or on zeolites or polystyrenes. Methods for the deposition of reactive components in mesoporous phases, zeolites and polystyrenes are known to persons skilled in the art and are suitable for being used without leaving the scope of protection of the patent claims.

The deposition of a Cu-(II)-oxygen adduct complex according to the present invention in a molecular sieve is named as an example: For that purpose, the molecular sieve is impregnated with a solution (acetone) of the corresponding [L-Cu]BAr$_4$ complex under inert gas atmosphere. The molecular sieve loaded with this [L-Cu]BAr$_4$ complex is subsequently exposed to an oxygen-containing atmosphere as described above, wherein the blue peroxo complex [L-Cu—O—O—Cu-L](BAr$_4$)$_2$ is formed on the surface of the molecular sieve beads.

EMBODIMENTS

Embodiment 1

Production of the Ligand
tris-(2-dimethylaminoethyl)amine (Me$_6$tren)

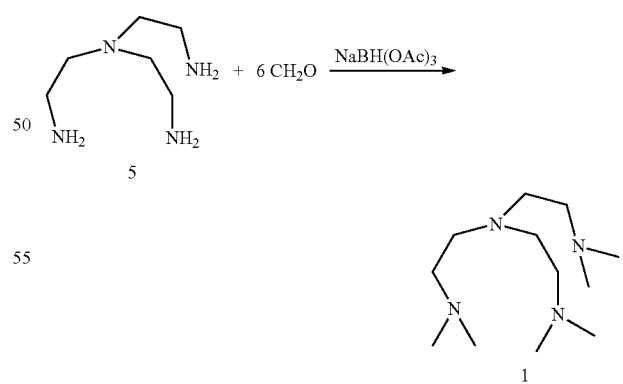

Me$_6$tren was produced as described in Britovsek et al., Inorg Chem 2005, 44, 8125-8134 and subsequently purified through distillation.

49 mL of an aqueous formaldehyde solution (37%, 660 mmol) was added to 3.0 mL (19.9 mmol) tren (5), 135 mL acetic acid and 600 mL acetonitrile and the mixture was stirred for one hour at room temperature. 10.0 g (13.4 mmol) sodium borohydride was slowly added to the solution cooled in the ice bath to 0° C. After 48 h of stirring at room temperature, the solvent was removed; the remainder was adjusted with 3 M sodium hydroxide solution to be strongly basic and extracted three times with 50 mL dichloromethane, respectively. The combined organic phases were dried over magnesium sulfate and the solvent was removed under vacuum. The remainder was dissolved in pentane, filtrated, and removed from the filtrate of the solvent in vacuum. The yellowish liquid was subsequently purified by means of Kugelrohr distillation. A colorless oil was obtained as the product (1).

$^1$H-NMR (CDCl$_3$): 2.55 (6H, t), 2.32 (6H, t), 2.16 (18H, s)

Embodiment 2

Production of the Ligand
bis-[2-aminoethyl-(2-pyridylmethyl)]amine
(Me$_4$apme)

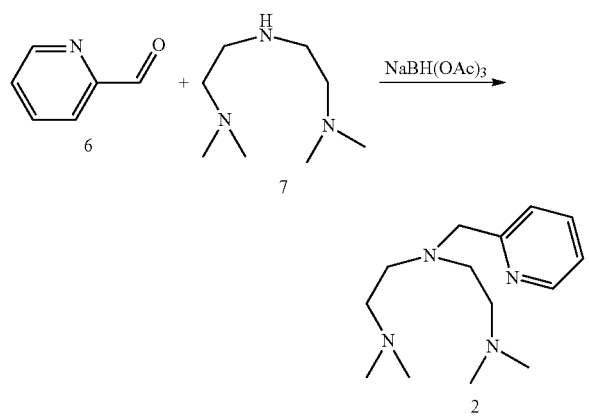

Me$_4$apme was produced as describe in Britovsek et al., Inorg Chem 2005, 44, 8125-8134 and subsequently purified through distillation.

1.96 g (12.3 mmol) bis[2-(dimethylamino)ethyl]amine (7) and 3.66 g (17.22 mmol) sodium triacetoborohydride were provided in 100 ml dichloromethane and, after the addition of 1.18 g (12.32 mmol) freshly distilled pyridine-2-carboxaldehyde (6), stirred for 12 hours at room temperature. The reaction was ended through the addition of 120 ml of 3 molar NaOH solution. The organic phase was separated, and the aqueous phase was extracted three times with 100 ml dichloromethane, respectively. The combined organic phases were dried over MgSO$_4$, and the solvent was removed under vacuum. The remainder was dissolved in 100 ml anhydrous THF, 0.6 g NaH (freed from mineral oil through washing with anhydrous petroleum ether) was added and stirred for 2 hours at room temperature. Subsequently, the solvent was removed in vacuum and the remainder was extracted three times with 50 ml pentane, respectively. The extracts were purified and the solvent was removed in vacuum. The yellow, viscous raw product was purified by means of at 130° C. A yellowish oil was obtained as the product (2).

$^1$H-NMR (CDCl$_3$): 8.47 (1H, d), 7.59 (1H, t), 7.43 (1H, d), 7.09 (1H, t), 3.75 (2H, s), 2.62 (4H, t), 2.38 (4H, t), 2.15 (12H, s)

Embodiment 3

Production of the Ligand
(2-aminoethyl)-bis(2-pyridylmethyl)amine
(Me$_2$uns-penp)

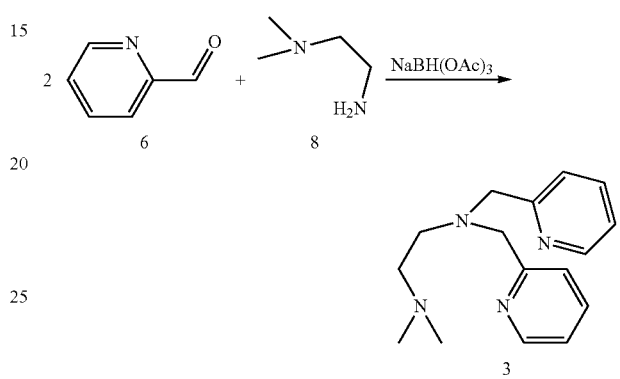

6.0 g (28.3 mmol) sodium triacetoborohydride was added under stirring to a mixture of 0.88 g (10 mmol) N,N-dimethylethane-1,2-diamine and 2.14 g (20 mmol) freshly distilled pyridine-2-carboxaldehyde in 60 ml 1,2-dichlorethane and stirred for a further 48 hours at room temperature. The reaction was ended through the addition of a 2 molar aqueous sodium hydroxide solution. The organic phase was separated, and the aqueous phase was extracted twice with 100 ml dichloromethane, respectively. The combined organic phases were washed with 100 ml saturated, aqueous saline solution and subsequently dried over NaSO$_4$. The solvents were removed under vacuum, and the brown oily remainder was extracted with diethylether. Subsequently, the solvent was removed in vacuum. A reddish oil was obtained as the product (3).

$^1$H-NMR (CDCl$_3$): 8.52 (2H, d), 7.65 (2H, t), 7.53 (2H, d), 7.14 (2H, m), 3.86 (4H, s), 2.71 (2H, t), 2.48 (2H, t), 2.17 (6H, s)

Embodiment 4

Production of the Ligand
tris-[(2-pyridyl)-methyl]amine (tmpa)

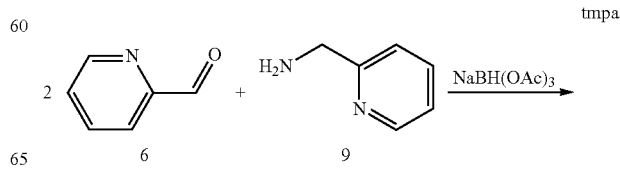

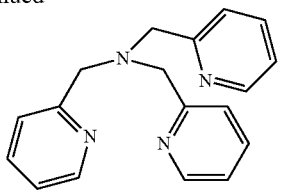

4

4 mL (42.0 mmol) freshly distilled pyridine-2-carbaldehyde (6) was added to a mixture of 2.16 g (20.0 mmol) 2-(aminomethyl)pyridine (9) and 12.6 g (214 mmol) sodium triacetoxyborohydride in 300 mL dichloromethane. After the yellowish mixture was stirred for 18 h at room temperature, a saturated solution of sodium hydrogen carbonate was added. The mixture was stirred 15 min at room temperature, extracted twice with ethyl acetate and the combined organic phases were dried over magnesium sulfate. The solvent was removed and the yellow, viscous remainder was extracted three times with petroleum ether. The combined organic phases were freed from the solvent in vacuum. A yellowish solid was obtained as the product (4).

$^1$H-NMR (CDCl$_3$): 8.55 (3H, d), 7.84 (3H, t), 7.79 (3H, d), 7.24 (3H, m), 3.87 (6H, s)

Embodiment 5

Production of [Cu(Me$_6$tren)]BPh$_4$

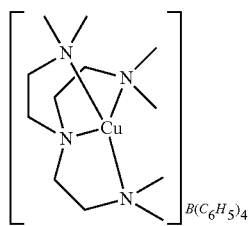

10

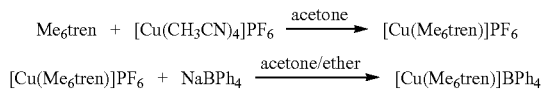

0.20 g (0.87 mmol) Me$_6$tren (1) was dissolved in approx. 2 ml acetone and a solution of 0.30 g (0.81 mmol) [Cu(CH$_3$CN)$_4$]PF$_6$ (tetrakis(acetonitrile)copper(I)-hexafluorophosphate) in approx. 4 ml acetone was added slowly under constant stirring. A solution of 0.28 g (0.82 mmol) NaBPh$_4$ (sodium tetraphenylborate) in approx. 2 mL acetone was added subsequently to the colorless, complex solution thus obtained, for the replacement of anions. For the preparation of the solid, the complex solution was added to 20 ml diethylether. The voluminous solid of [Cu(Me$_6$tren)]BPh$_4$ (10) obtained was dried in vacuum. 0.48 g (96.6%) of a colorless powder was obtained as the product.

All work was carried out in an argon box. It is possible, however, to carry out all work with the Schlenk technique under argon or nitrogen as well.

The complex [Cu(Me$_6$tren)]BPh$_4$ is shown in FIG. 1.

The results of the crystal structure analysis of [Cu(Me$_6$tren)]BPh$_4$ are shown in FIG. 2.

Embodiment 6

Production of [Cu(Me$_4$apme)]BPh$_4$

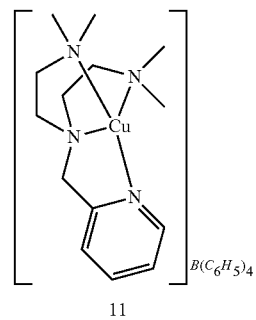

11

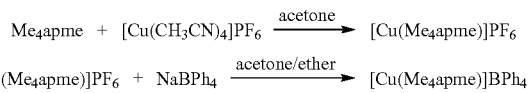

0.20 g (0.80 mmol) Me$_4$apme (2) was dissolved in approx. 2 ml acetone and a solution of 0.29 g (0.78 mmol) [Cu(CH$_3$CN)$_4$]PF$_6$ (tetrakis(acetonitrile)copper(I)-hexafluorophosphate) in approx. 4 ml acetone was added slowly under constant stirring. For the replacement of anions, a solution of 0.28 g (0.82 mmol) NaBPh$_4$ (sodium tetraphenylborate) in approx. 2 mL acetone was added subsequently to the yellow, complex solution thus obtained. For the preparation of the solid, the complex solution was added to 20 ml diethylether. The voluminous solid of [Cu(Me$_4$apme)]BPh$_4$ (11) obtained was dried in vacuum. 0.44 g (89.1%) of a yellow powder was obtained.

All work was carried out in an argon box. It is possible, however, to carry out all work with the Schlenk technique under argon or nitrogen as well.

Embodiment 7

Production of [Cu(Me$_2$uns-penp)]BPh$_4$

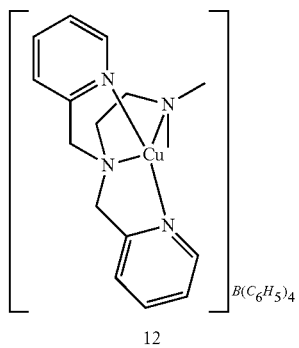

12

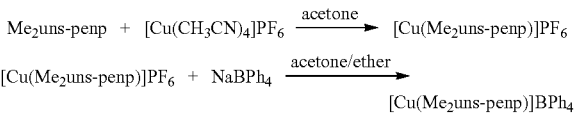

0.20 g (0.74 mmol) Me₂uns-penp (3) was dissolved in approx. 2 ml acetone and a solution of 0.27 g (0.72 mmol) [Cu(CH₃CN)₄]PF₆ (tetrakis(acetonitrile)copper(I)-hexafluorophosphate) in approx. 4 ml acetone was added slowly under constant stirring. For the replacement of anions, a solution of 0.28 g (0.82 mmol) NaBPh₄ (sodium tetraphenylborate) in approx. 2 mL acetone was added subsequently to the orange, complex solution thus obtained. For the preparation of the solid, the complex solution was added to 20 ml diethylether. The voluminous solid of [Cu(Me₂uns-penp)]BPh₄ (12) obtained was dried in vacuum. 0.46 g (97.8%) of a yellow powder was obtained as the product.

All work was carried out in an argon box. It is possible, however, to carry out all work with the Schlenk technique under argon or nitrogen as well.

The complex [Cu(Me₂uns-penp)]BPh₄ is shown in FIG. 3.

Embodiment 8

Production of [Cu(tmpa)]BPh₄

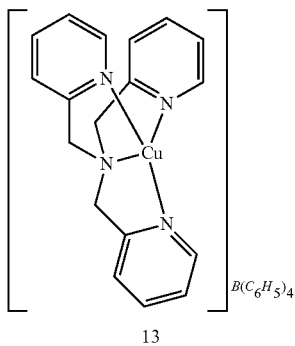

13

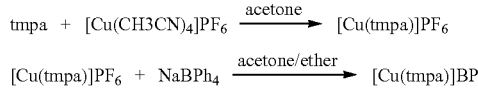

0.20 g (0.69 mmol) tmpa (4) was dissolved in approx. 2 ml acetone and a solution of 0.25 g (0.67 mmol) [Cu(CH₃CN)₄]PF₆ (tetrakis(acetonitrile)copper(I)-hexafluorophosphate) in approx. 4 ml acetone was added slowly under constant stirring. For the replacement of anions, a solution of 0.28 g (0.82 mmol) NaBPh₄ (sodium tetraphenylborate) in approx. 2 mL acetone was added subsequently to the orange, complex solution thus obtained. For the preparation of the solid, the complex solution was added to 20 ml diethylether. The voluminous solid of [Cu(tmpa)]BPh₄ (13) obtained was dried in vacuum. 0.41 g (90.9%) of a yellow powder was obtained as the product.

All work was carried out in an argon box. It is possible, however, to carry out all work with the Schlenk technique under argon or nitrogen as well.

The complex [Cu(tmpa)]BPh₄ is shown in FIG. 4.

Embodiment 9

Production of the peroxo complex [Cu₂(Me₆tren)₂(O₂)](BPh₄)₂

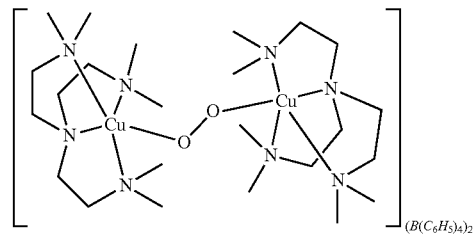

14

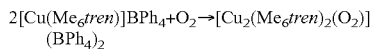

The freshly produced Cu(I) complex 10 was taken out of the argon box as a colorless powder under argon in a closed container. After opening the reaction vessel, oxygen gas (air is also possible) was added to the Cu(I) complex. Within seconds, the intensely blue-colored peroxo complex 14 is formed.

Alternative Preparation:

A colorless solution of the Cu(I) complex 10 in acetone or acetonitrile was taken out of the argon box under argon in a closed container. The solution was cooled down to −80° C. in an ethanol bath and reacted with oxygen gas (air is also possible). Within seconds, the intensely blue-colored peroxo solution is formed. Through the addition of cold (−80° C.) diethylether, the peroxo complex precipitates out as a voluminous solid. Through filtration and drying (with oxygen gas) at −80° C., the peroxo complex (14) is subsequently able to be isolated stable at room temperature.

FIG. 5 shows the UV-VIS spectrum of the peroxo complex 14.

Embodiment 10

Production of the peroxo complex [Cu₂(Me₄apme)₂(O₂)](BPh₄)₂

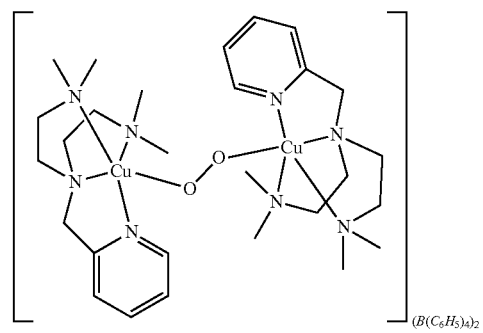

15

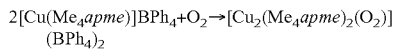

The freshly produced Cu(I) complex 11 was taken out of the argon box as a yellow powder under argon in a closed container. After opening the reaction vessel, oxygen gas (air is also possible) was added to the Cu(I) complex. Within seconds, the intensely blue-colored peroxo complex 15 is formed.

Alternative Preparation:

A yellow solution of the Cu(I) complex 11 in acetone or acetonitrile was taken out of the argon box under argon in a closed container. The solution was cooled down to −80° C. in an ethanol bath and reacted with oxygen gas (air is also possible).

Within seconds, the intensely blue-colored peroxo solution is formed. Through the addition of cold (−80° C.) diethylether, the peroxo complex precipitates out as a voluminous solid. Through filtration and drying (with oxygen gas) at −80° C., the peroxo complex (15) is subsequently able to be isolated stable at room temperature.

FIG. 6 shows the UV-VIS spectrum of the peroxo complex 15.

Embodiment 11

Production of the peroxo complex [$Cu_2(Me_2uns-penp)_2(O_2)$]KBPh$_4)_2$

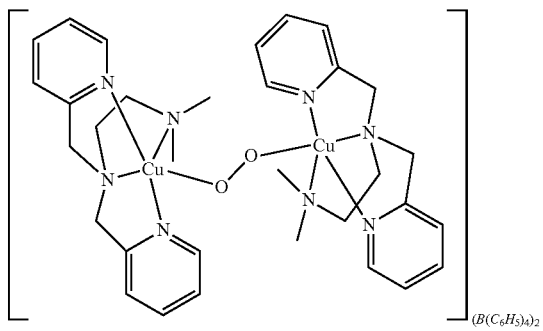

2[Cu(Me$_2$uns-penp)]BPh$_4$+O$_2$→[Cu$_2$(Me$_2$uns-penp)$_2$(O$_2$)](BPh$_4$)$_2$ A yellow solution of the Cu(I) complex 12 in acetone or acetonitrile was taken out of the argon box under argon in a closed container. The solution was cooled down to −80° C. in an ethanol bath and reacted with oxygen gas (air is also possible).

Within seconds, the intensely blue-colored peroxo solution is formed. Through the addition of cold (−80° C.) diethylether, the peroxo complex precipitates out as a voluminous solid. Through filtration and drying (with oxygen gas) at −80° C., the peroxo complex (16) is subsequently able to be isolated stable at room temperature.

FIG. 7 shows the UV-VIS spectrum of the peroxo complex 16.

Embodiment 12

Production of the peroxo complex [$Cu_2(tmpa)_2(O_2)$](BPh$_4)_2$

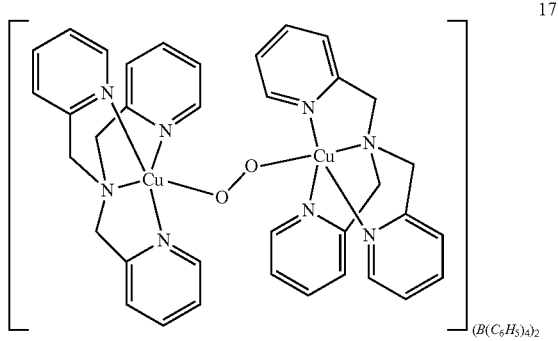

2[Cu(tmpa)]BPh$_4$+O$_2$→[Cu$_2$(tmpa)$_2$(O$_2$)](BPh$_4$)$_2$

The freshly produced Cu(I) complex 13 was taken out of the argon box as a yellow powder under argon in a closed container. After opening the reaction vessel, oxygen gas (air is also possible) was added to the Cu(I) complex. Within seconds, the intensely blue-colored peroxo complex 17 is formed.

Alternative Preparation:

A yellow solution of the Cu(I) complex 17 in acetone or acetonitrile was taken out of the argon box under argon in a closed container. The solution was cooled down to −80° C. in an ethanol bath and reacted with oxygen gas (air is also possible). Within seconds, the intensely blue-colored peroxo solution is formed. Through the addition of cold (−80° C.) diethylether, the peroxo complex precipitates as a voluminous solid. Through filtration and drying (with oxygen gas) at −80° C., the peroxo complex (17) is subsequently able to be isolated stable at room temperature.

FIG. 8 shows the UV-VIS spectrum of the peroxo complex 17.

Embodiment 13

Oxidation of Benzene to Phenol

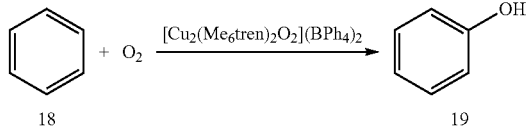

For the duration of approx. two days, the catalyst is reacted with benzene and oxygen in a closed glass at room temperature. For that purpose, a small, open glass is filled with benzene. In a second, higher and closable screw top glass, [Cu$_2$(Me$_6$tren)$_2$O$_2$](BPh$_4$)$_2$ is added. The smaller glass containing benzene is placed onto the catalyst, the gas space is filled with oxygen and the larger glass closed with a screw top.

After some time, benzene steam condensates on the catalyst surface and reacts to phenol. After two days, the benzene-filled glass is removed and the catalyst is washed with diethylether. In the etheric solution, phenol is able to be detected/verified through GC-MS.

FIG. 9 shows the GC analysis of the etheric solution.
FIG. 10 shows the GC-MS analysis of the etheric solution.

BRIEF DESCRIPTION OF THE DRAWINGS

FIG. 1 shows an ORTEP representation of [Cu(Me$_6$tren)]BPh$_4$. The representation of the anion (tetraphenylborate) and the hydrogen atoms was omitted due to clarity. (thermal ellipsoids with 50% spatial probability)

The imaging of the monocrystal was carried out through the omega scan technique with a Siemens SMART CCD 1000 diffractometer with the use of Mo K$_\alpha$-radiation ([α]=0.71073 angstrom) and a graphite monochromator. The program SADABS (Siemens Area Detector Absorption Correction, Siemens) was used for the absorption correction. The program package SHELX97 was used for determining the structure (direct methods) and refinement. The positions of all hydrogen atoms were calculated geometrically. All non-hydrogen atoms were anisotropically refined.

Figure 2:
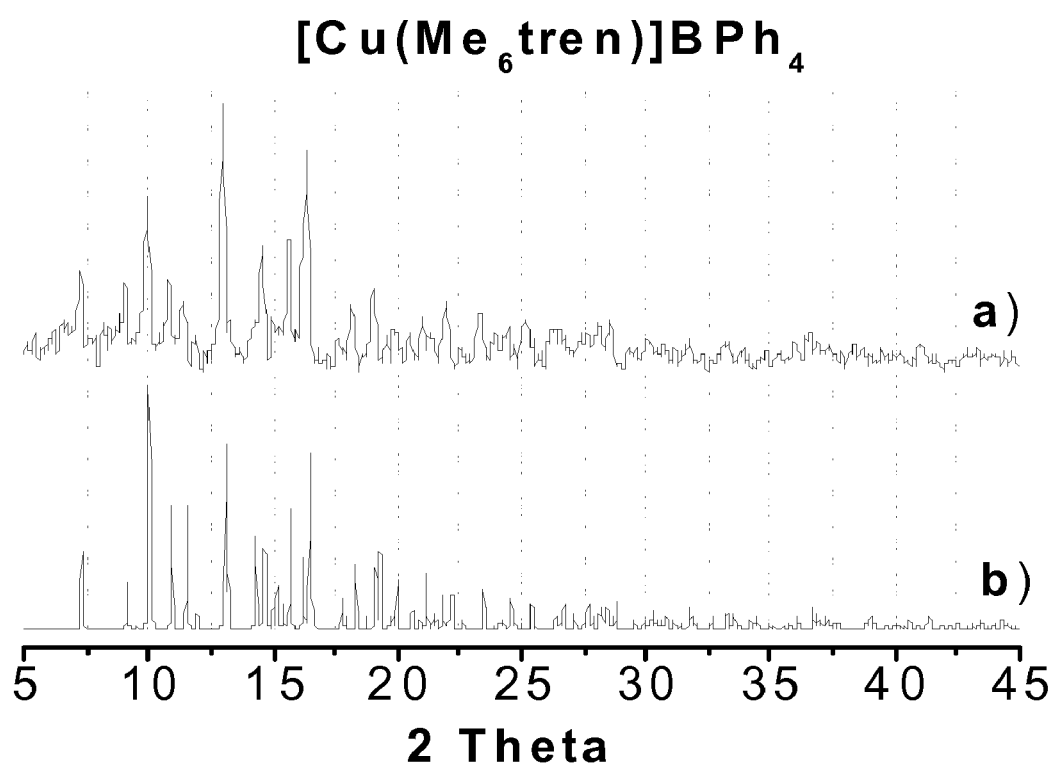

FIG. 2
Crystal structure analysis of [Cu(Me$_6$tren)]BPh$_4$:
a) shows the powder diffractogram of the powder,
b) shows the powder diffractogram simulated from the monocrystal The imaging of the powder was carried out through the capillary technique with a STOE Stadi-P diffractometer with an IP-PS (image plate position sensitive) detector.

Cu K$_\alpha$-radiation ([α]=1.54056 angstrom) and a germanium-monochromator were used.

Figure 1:
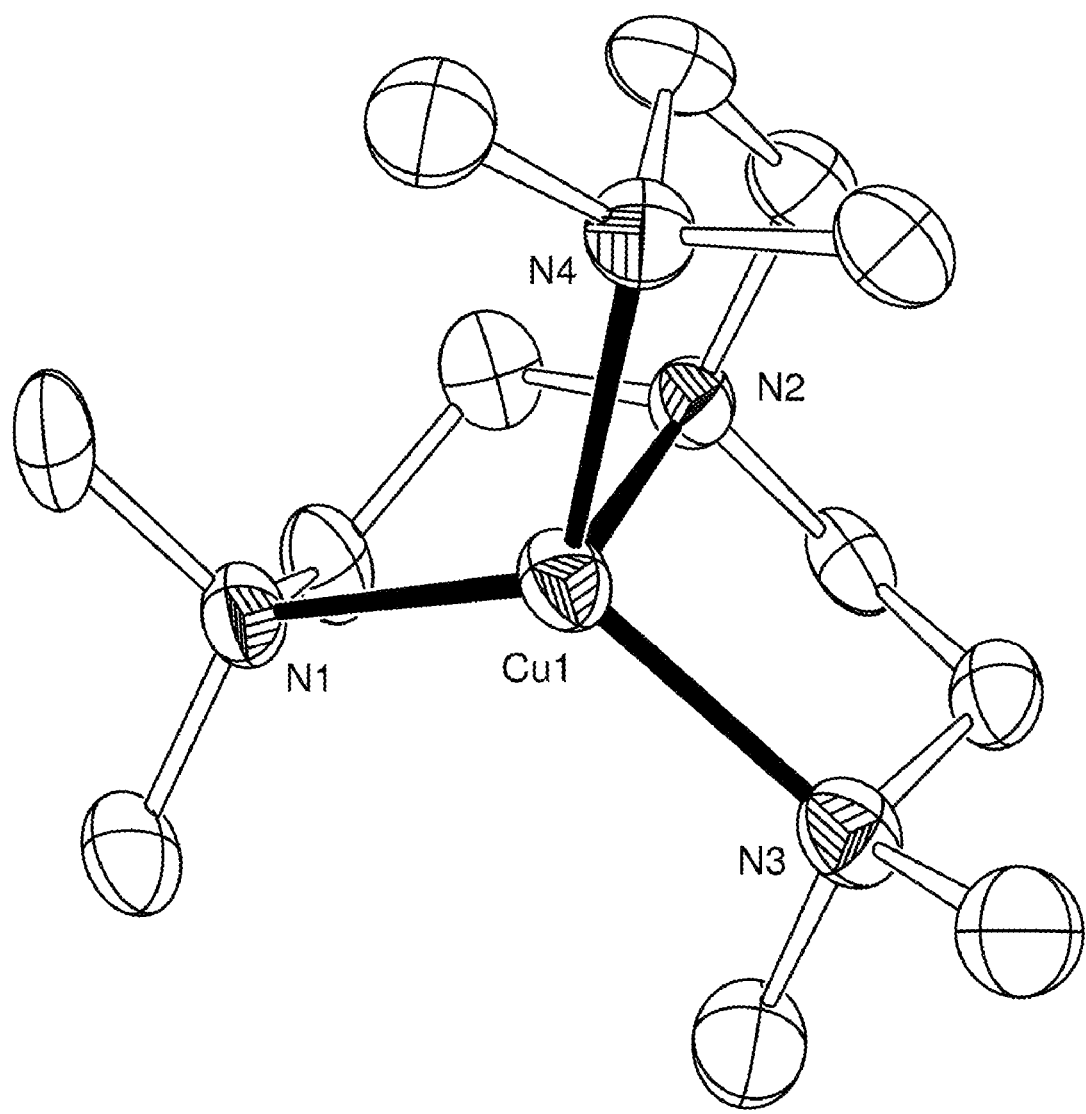
FIG. 1

The monocrystal describe in FIG. 1 was used for the simulation of the powder diffractogram. The simulation was carried out with the PowderCell 2.4 program.

FIG. 3

Figure 3:
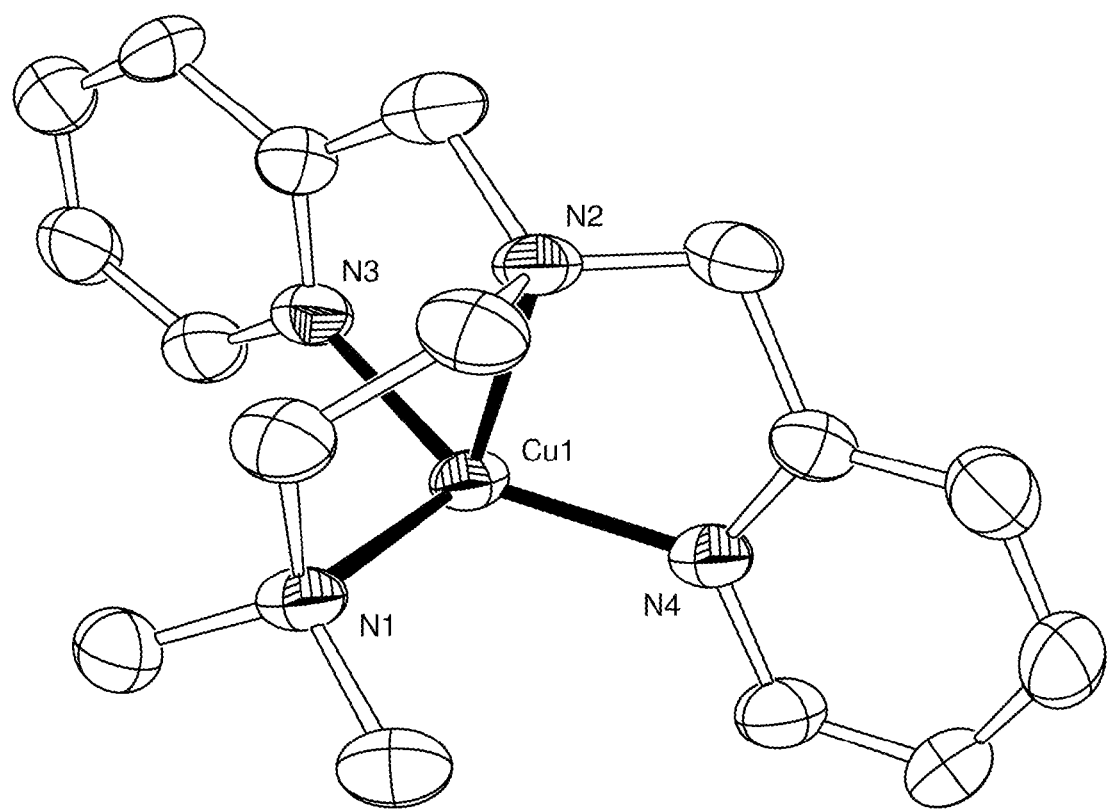

FIG. 3 shows an ORTEP representation of [Cu(Me$_2$uns-penp)]BPh$_4$. The representation of the anion (tetraphenylborate) and the hydrogen atoms was omitted due to clarity. (thermal ellipsoids with 50% spatial probability)

The imaging of the monocrystal was carried out via Mo K$_\alpha$-radiation ([α]=0.71096 angstrom) and a graphite monochromator with a STOE IPDS diffractometer with connected low-temperature system (Karlsruher Glastechnisches Werk). No absorption correction was carried out. The program package SHELX97 was used for determining the structure (direct methods) and refinement. The positions of all hydrogen atoms were calculated geometrically. All non-hydrogen atoms were anisotropically refined.

FIG. 4

Figure 4:
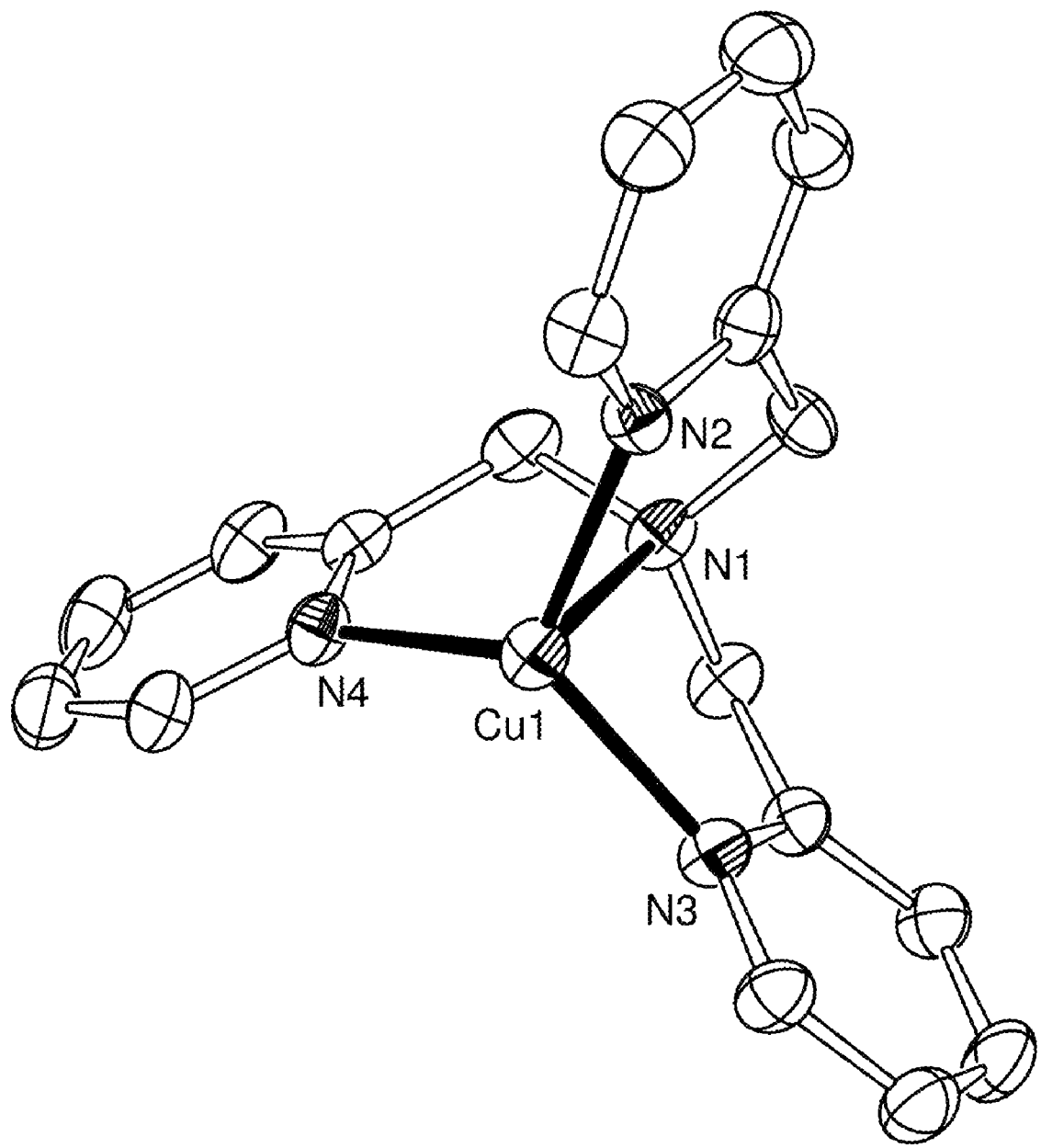

FIG. 4 shows an ORTEP representation of [Cu(tmpa)]BPh$_4$. The representation of the anion (tetraphenylborate) and the hydrogen atoms was omitted due to clarity. (thermal ellipsoids with 50% spatial probability)

The imaging of the monocrystal was carried out via Mo K$_\alpha$-radiation ([α]=0.71096 angstrom) and a graphite monochromator with a STOE IPDS diffractometer with connected low-temperature system (Karlsruher Glastechnisches Werk). No absorption correction was carried out. The program package SHELX97 was used for the structure solution (direct methods) and refinement. The positions of all hydrogen atoms were calculated geometrically. All non-hydrogen atoms were anisotropically refined.

Figure 5:
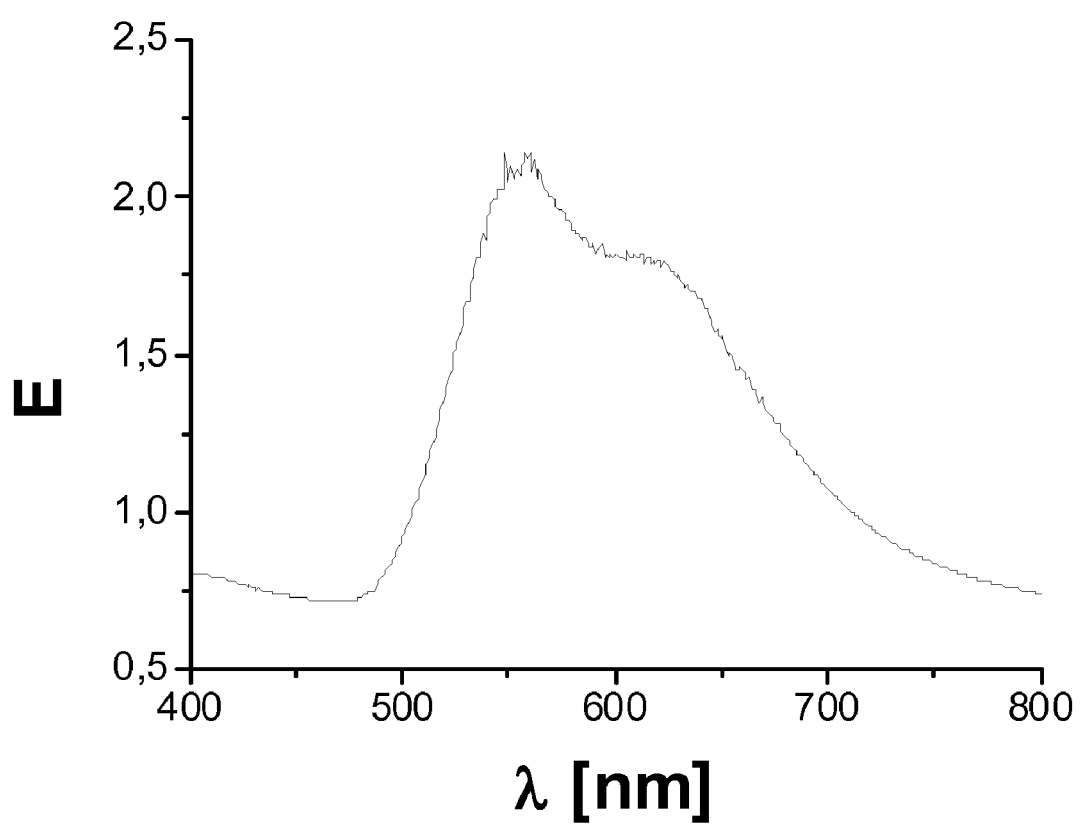
Figure 6:
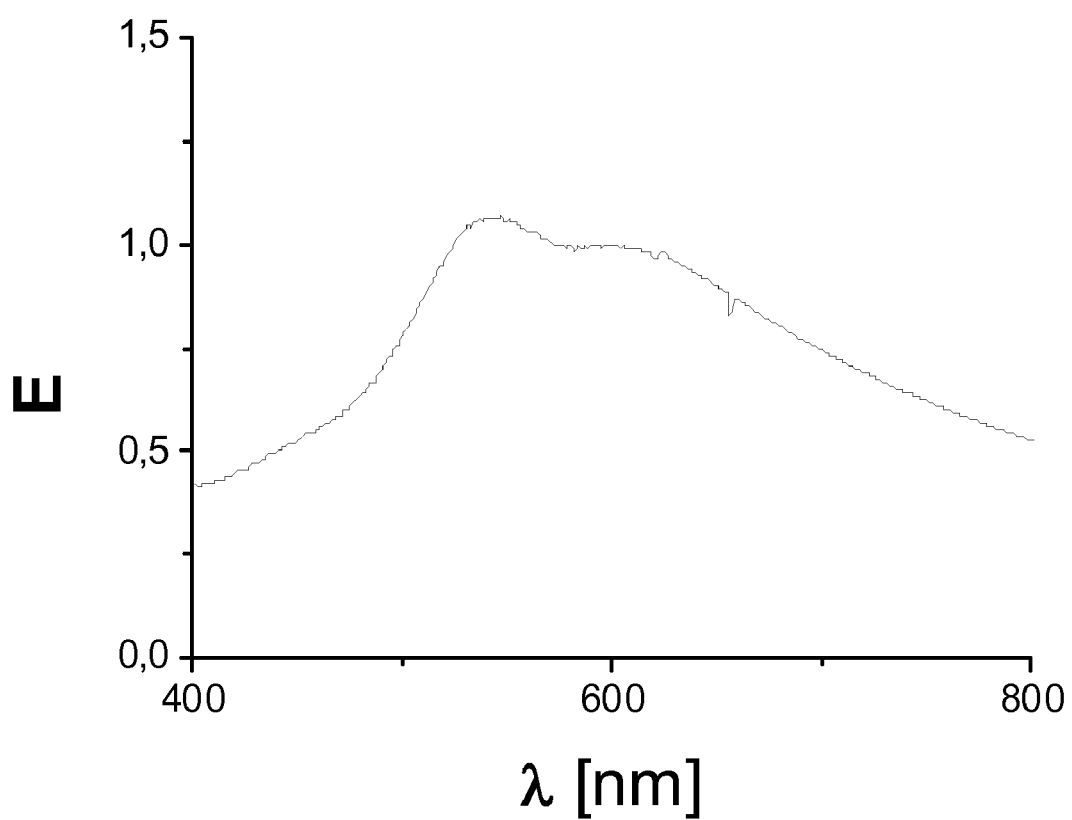
Figure 7:
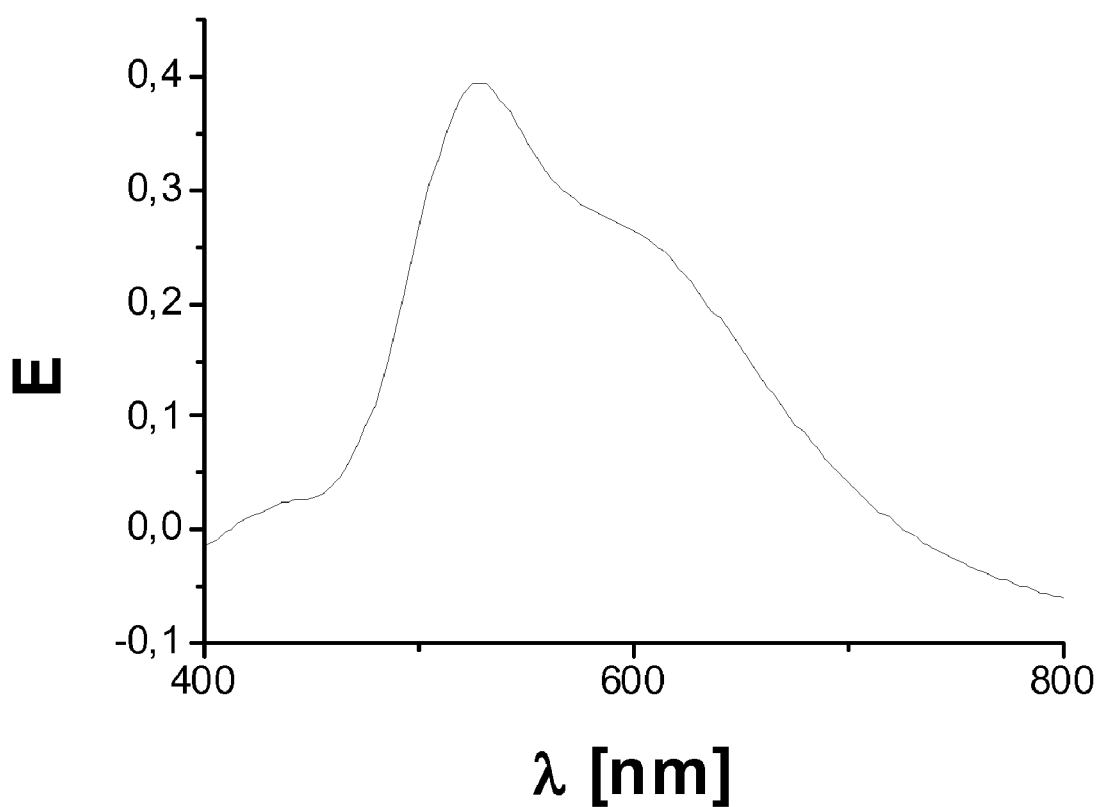
Figure 8:
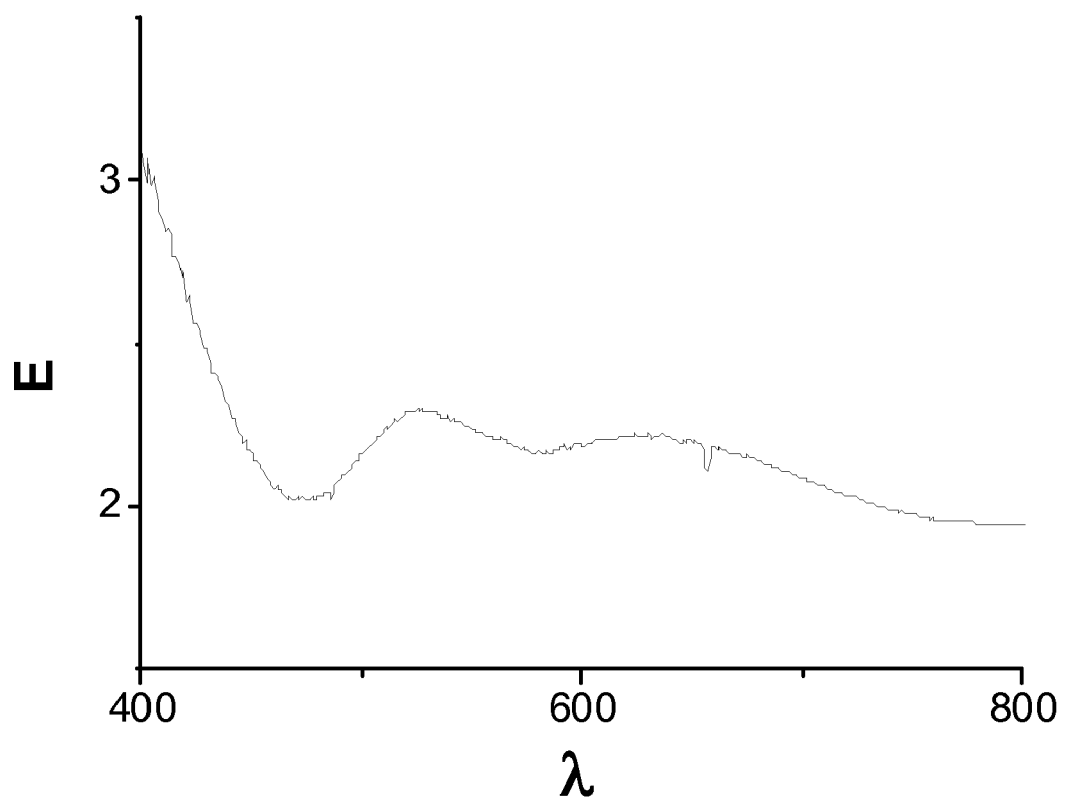
Figure 9:
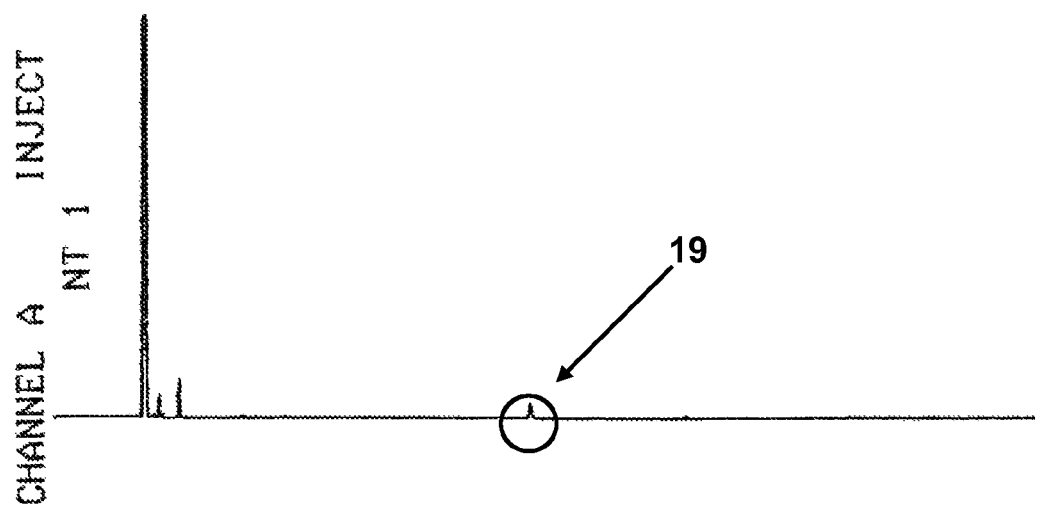

FIG. 5
UV-VIS spectrum of the peroxo complex [Cu$_2$(Me$_6$tren)$_2$(O$_2$)](BPh$_4$)$_2$. The spectrum shows the typical Cu—O$_2$ charge-transfer double band.
Temperature: −60° C.
Solvent: acetone
E: extinction
λ: wavelength FIG. 6
UV-VIS spectrum of the peroxo complex [Cu$_2$(Me$_4$apme)$_2$(O$_2$)](BPh$_4$)$_2$. The spectrum shows the typical Cu—O$_2$ charge-transfer double band.
Temperature: −60° C.
Solvent: acetone
E: extinction
λ: wavelength FIG. 7
UV-VIS spectrum of the peroxo complex [Cu$_2$(Me$_2$uns-penp)$_2$(O$_2$)](BPh$_4$)$_2$. The spectrum shows the typical Cu—O$_2$ charge-transfer double band.
Temperature: −80° C.
Solvent: acetone
E: extinction
λ: wavelength FIG. 8
UV-VIS spectrum of the peroxo complex [Cu$_2$(tmpa)$_2$(O$_2$)](BPh$_4$)$_2$. The spectrum shows the typical Cu—O$_2$ charge-transfer double band.
Temperature: 25° C.
Solvent: acetone
E: extinction
λ: wavelength FIG. 9
GC analysis of the etheric solution from embodiment 13.
GC device: Carlo Erba Instruments HRGC 530D Mega Series; column: UP5; gas mixture: nitrogen/air; gas flow: 200 ml/min The signal for phenol (19) is detected at a retention time of 4.17 min.

FIG. 10
GC-MS analysis of the etheric solution from embodiment 13.
GC device: HP 5890; gas mixture: nitrogen/air; gas flow: 200 ml/min; MS device: quadrupole MS HP MSD 5971 (EI)

Figure 10A:
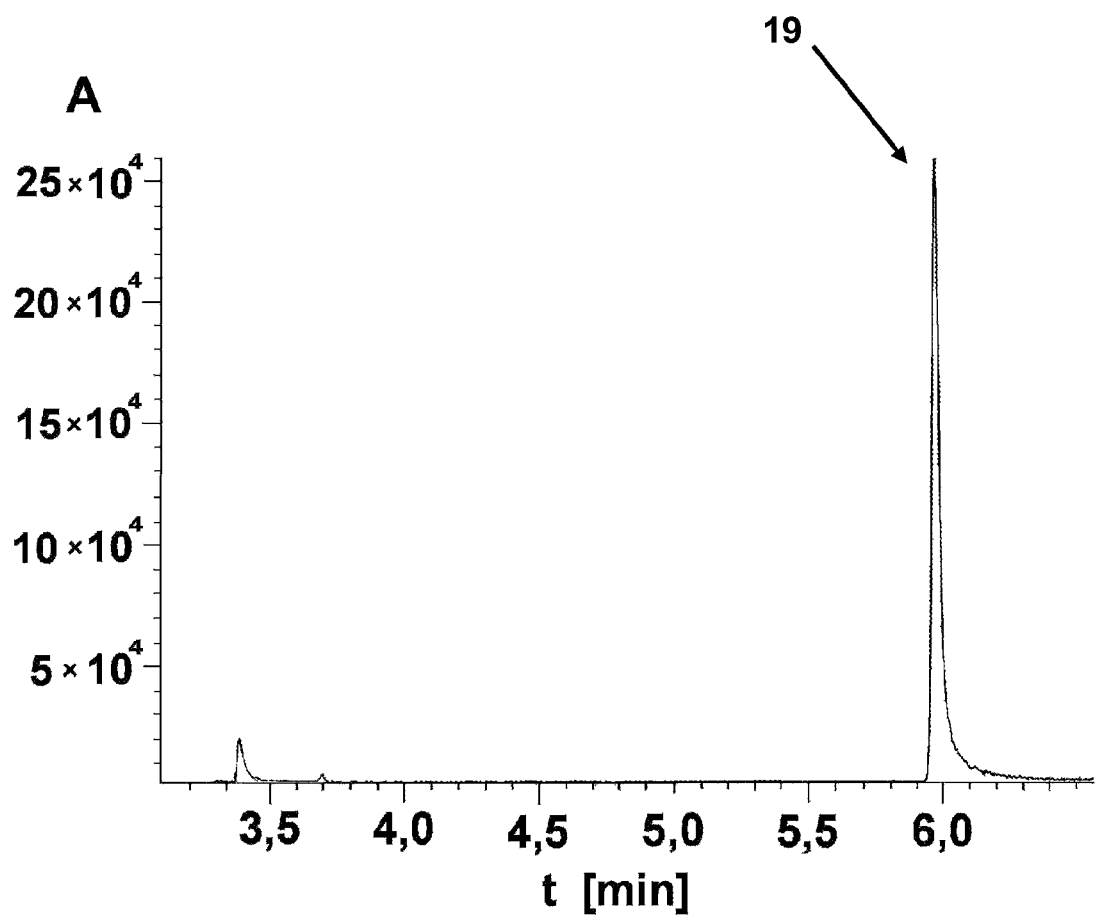
Figure 10B:
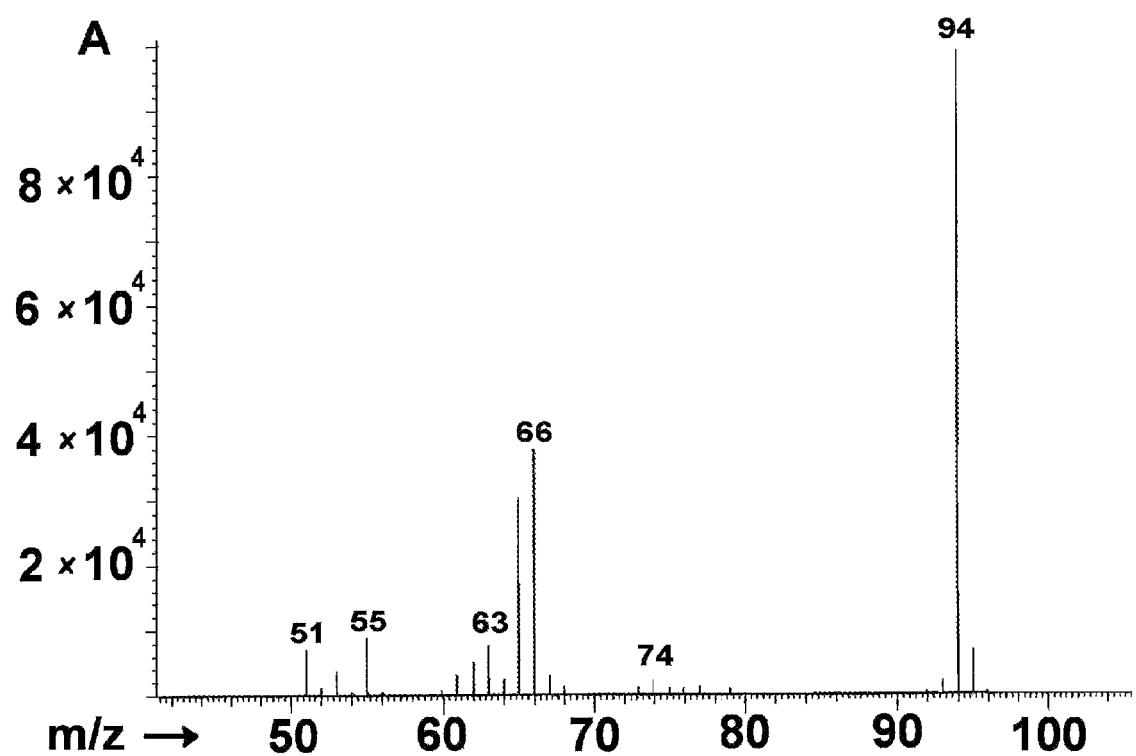
Figure 11:
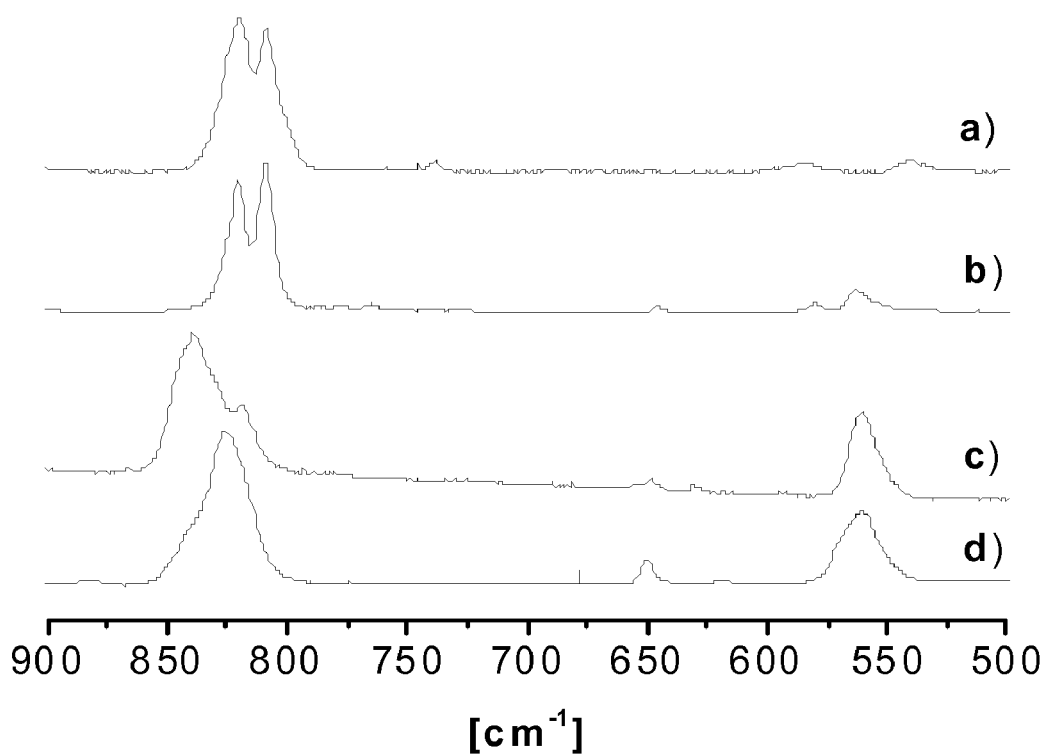

FIG. 10a
Phenol (19) is detected at a retention time of 5.98 min in gas chromatogram.
t [min]: retention time in minutes
A: abundance=signal intensity FIG. 10b
MS analysis of the phenol peak shows the typical isotope pattern for phenol.
m/z: quotient of mass divided by the charge of the detected ions
A: abundance=signal intensity FIG. 11
Resonance Raman spectra of the peroxo complex
a) [Cu$_2$(Me$_6$tren)$_2$(O$_2$)](BPh$_4$)$_2$
b) [Cu$_2$(Me$_4$apme)$_2$(O$_2$)](BPh$_4$)$_2$
c) [Cu$_2$(Me$_2$uns-penp)$_2$(O$_2$)](BPh$_4$)$_2$
d) [Cu$_2$(tmpa)$_2$(O$_2$)](BPh$_4$)$_2$ The spectra of the measurements of the solids show the typical Cu—O and O—O stretching vibration at around 550 and 800 cm$^{-1}$.
Excitation wavelength: 568.2 nm
cm$^1$: wave numbers

The invention claimed is:
1. Copper-(II)-oxygen adduct complexes of the general formula

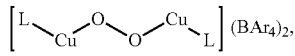 (I)

wherein
BAr$_4$ stands for a tetraarylborate anion, selected from tetraphenylborate and tetrakis(3,5-trifluoromethyl)phenylborate
and
L represents a tripodal tetradentate ligand, wherein
a) each of the four binding sites of the tripodal tetradentate ligand is a nitrogen atom, and
b) three podal nitrogen-containing ligands are bound to the central nitrogen atom, and
c) the tripodal tetredentate ligand L is a ligand of the general formula

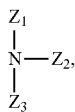 (II)

wherein $Z_1$, $Z_2$ and $Z_3$ are selected independently of one another from each of the three podal nitrogen-containing ligands comprises, independently of one another, an aliphatic amine or a nitrogen-containing heteroaromatic compound, and
d) a bridge of one to four carbon atoms is located between the central nitrogen atom and the nitrogen atom of each of the podal ligands, wherein
the bridge of one to four carbon atoms exclusively comprises sp$^3$-hybridized aliphatic carbon atoms, if the podal ligand is an aliphatic amine, and the aliphatic amine is bound to an alkylene group of one to four carbon atoms, according to the formula

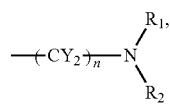 (III)

wherein Y, n, $R_1$, and $R_2$ have the following meanings and, for each of the groups $Z_1$, $Z_2$ and $Z_3$ are suitable for being selected independently of one another:
Y=H or F,
n=1, 2, 3, 4, and
$R_1$ and $R_2$ are selected independently of one another from
—H, —CH$_3$, —CH$_2$CH$_3$, —CH$_2$CH$_2$CH$_3$, —CH(CH$_3$)$_2$, C(CH$_3$)$_3$,
—CF$_3$, —CF$_2$CF$_3$, —CF$_2$CF$_2$CF$_3$, —CF(CF$_3$)$_2$, C(CF$_3$)$_3$,
wherein, for the case that one of the two groups $R_1$ or $R_2$ represents —C(CH$_3$)$_3$ or —C(CF$_3$)$_3$, the other group $R_1$ or $R_2$ is selected from
—H, —CH$_3$ and CF$_3$
phenyl, pentafluorophenyl, methylphenyl, dimethylphenyl, trifluoromethylphenyl, (bis-trifluoromethyl)phenyl, or
if the podal ligand is a nitrogen-containing heteroaromatic compound, the bridge of one to four carbon atoms comprises exactly one sp$^2$-hybridized carbon atom, wherein this sp$^2$-hybridized carbon atom is part of the heterocyclic aromatic compound and is located in the 2-position to at least one nitrogen atom of the heterocyclic ring.

2. Copper-(II)-oxygen adduct complexes according to claim 1, wherein the
aliphatic amine, which is bound to an alkylene group of one to four carbon atoms, is according to the formula

 (III)

and the nitrogen-containing heteroaromatic compound, which is bound in the 2-position to at least one of its nitrogen atoms to an alkylene group of zero to three carbon atoms, is according to

 (IV)

so that the aromatic sp$^2$-hybridized carbon atom, which is located in the 2-position to at least one nitrogen atom of the heteroaromatic compound, forms, together with the alkylene group —(CY$_2$)$_m$—, a bridge of one to four carbon atoms between the central nitrogen atom of the ligand L and the at least one nitrogen atom of the heteroaromatic compound,
wherein,
m and Het have the following meanings
m=0, 1, 2, 3,
and Het is a nitrogen-containing heteroaromatic, selected from

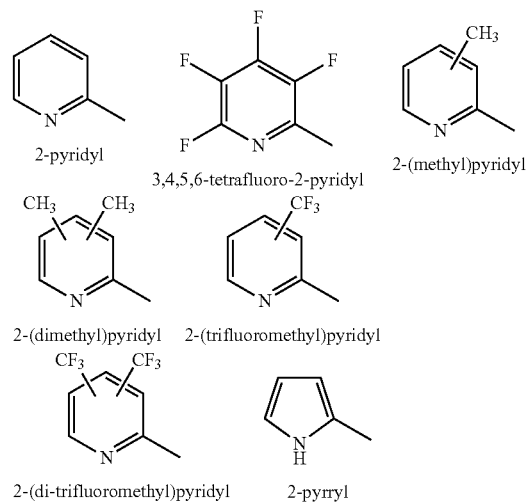

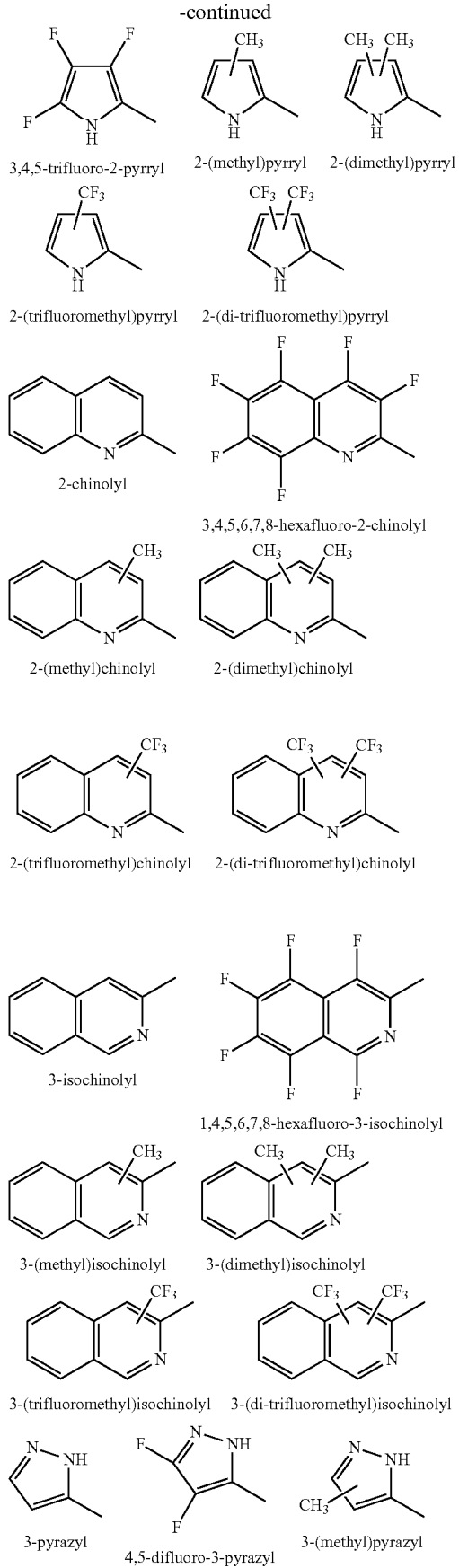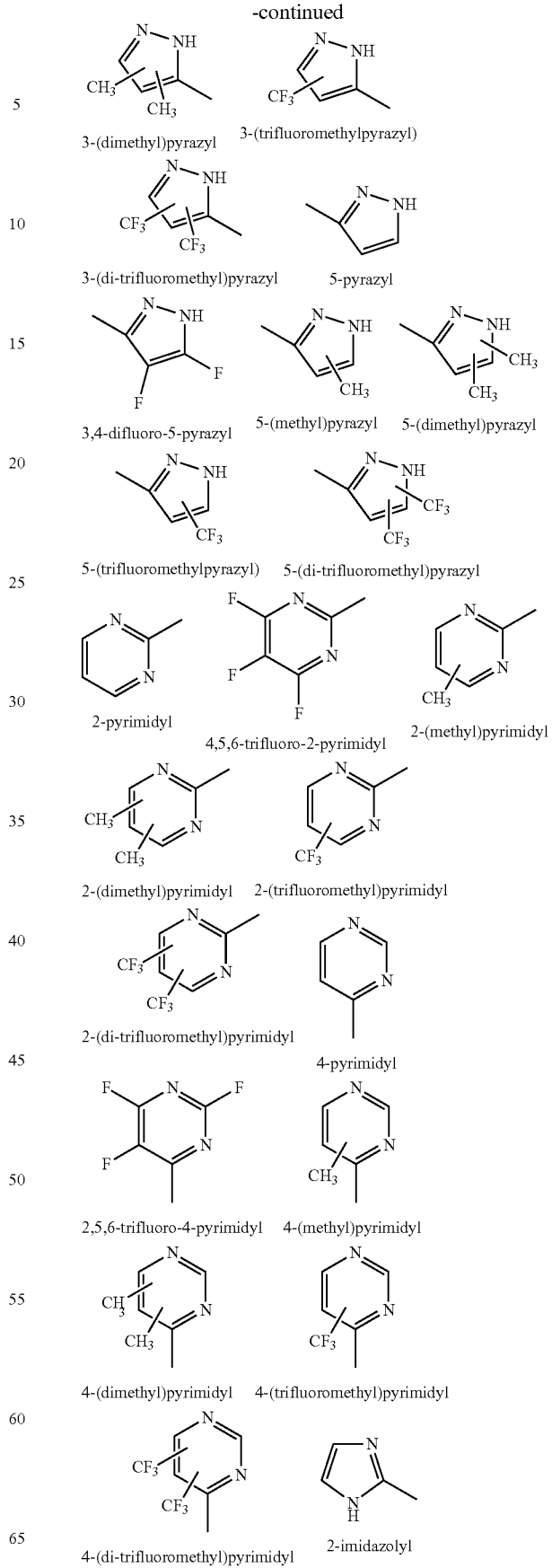

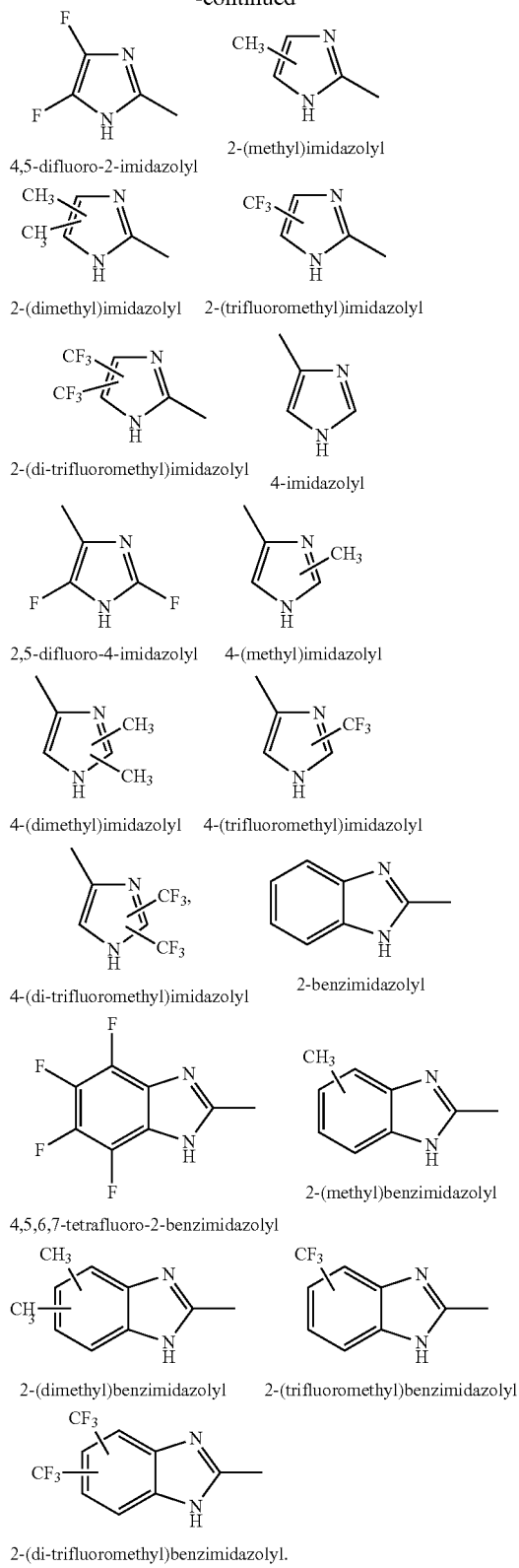

3. Copper-(II)-oxygen adduct complexes according to claim 1, wherein the aliphatic amine, which is bound to an alkylene group of one to four carbon atoms, is according to the formula

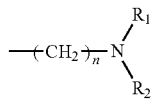

(V)

and the nitrogen-containing heteroaromatic compound, which is bound in the 2-position to at least one of its nitrogen atoms to an alkylene group of zero to three carbon atoms is according to the formula

(VI)

wherein m and Het have the following meanings m=0, 1, 2, 3, and

Het is a nitrogen-containing heteroaromatic, selected from

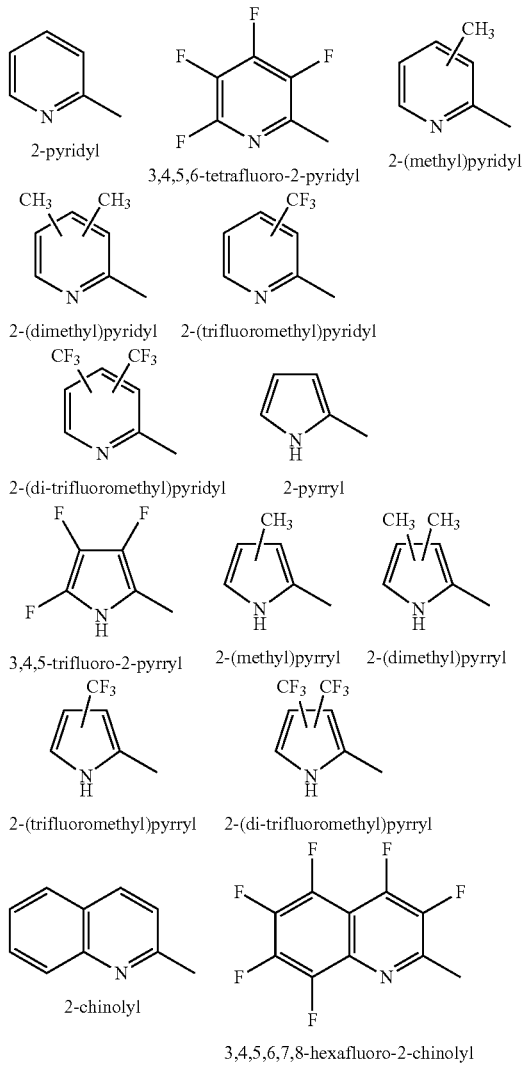

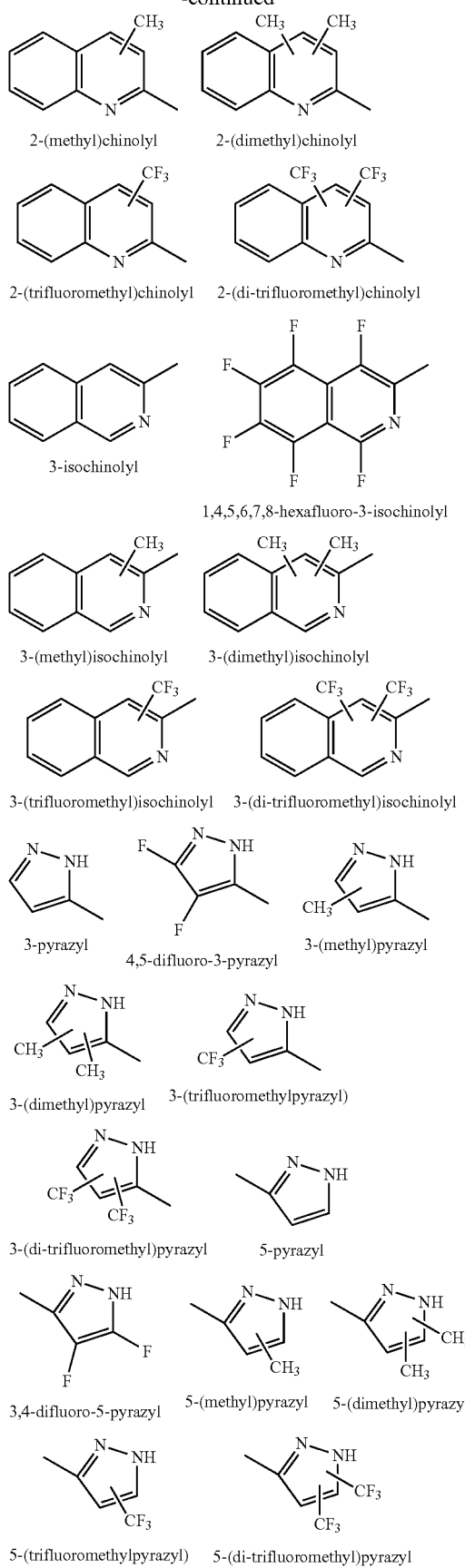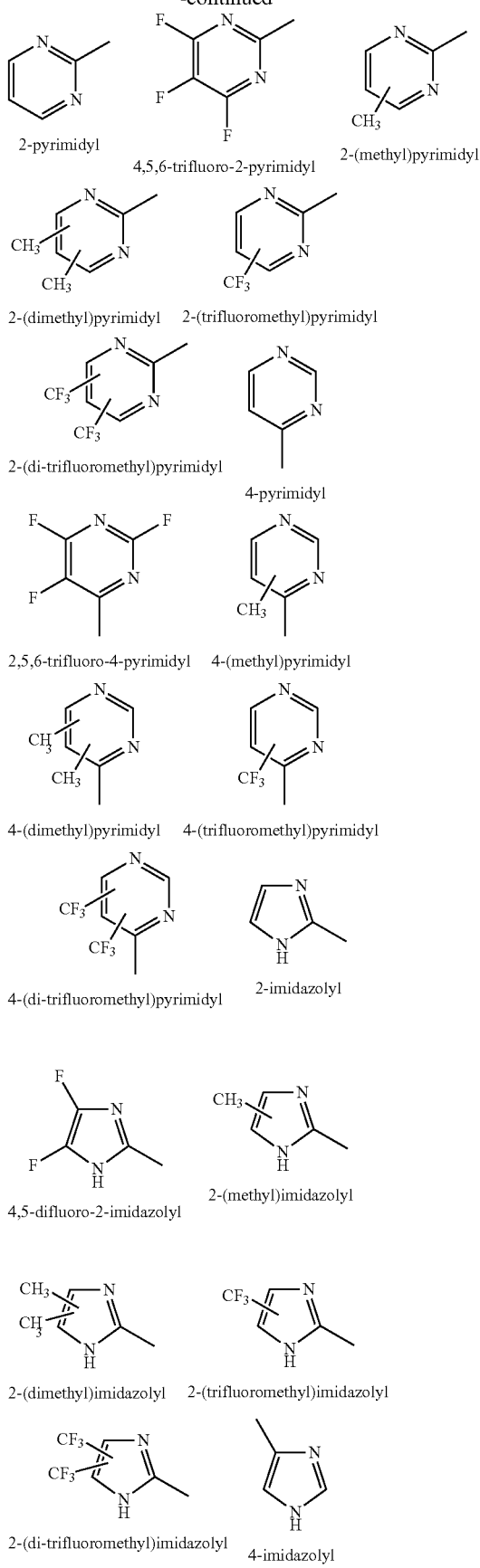

-continued

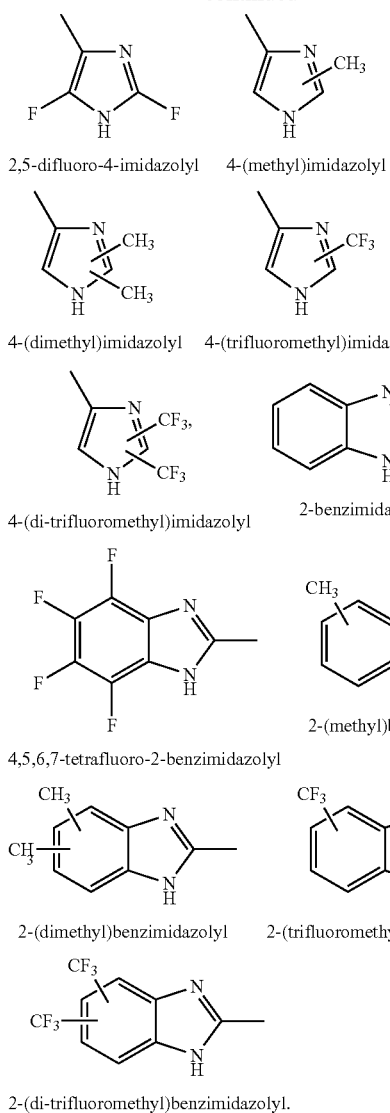

2,5-difluoro-4-imidazolyl   4-(methyl)imidazolyl 4-(dimethyl)imidazolyl   4-(trifluoromethyl)imidazolyl 4-(di-trifluoromethyl)imidazolyl   2-benzimidazolyl 4,5,6,7-tetrafluoro-2-benzimidazolyl   2-(methyl)benzimidazolyl 2-(dimethyl)benzimidazolyl   2-(trifluoromethyl)benzimidazolyl 2-(di-trifluoromethyl)benzimidazolyl.

and wherein, in the case that one of the two groups $R_1$ or $R_2$ represents —$C(CH_3)_3$ or —$C(CF_3)_3$, the other group $R_1$ or $R_2$ is selected from —H, —$CH_3$ and $CF_3$.

4. Copper-(II)-oxygen adduct complexes according to claim 1, wherein the aliphatic amine, which is bound to an alkylene group of two carbon atoms, is according to the formula and

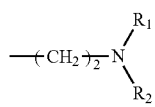

(VII)

the nitrogen-containing heteroaromatic compound, which is bound in the 2-position to at least one of its nitrogen atoms to a methylene group, is according to the formula —$CH_2$—Het,    (VIII)

wherein

Het is a nitrogen-containing heteroaromatic, selected from

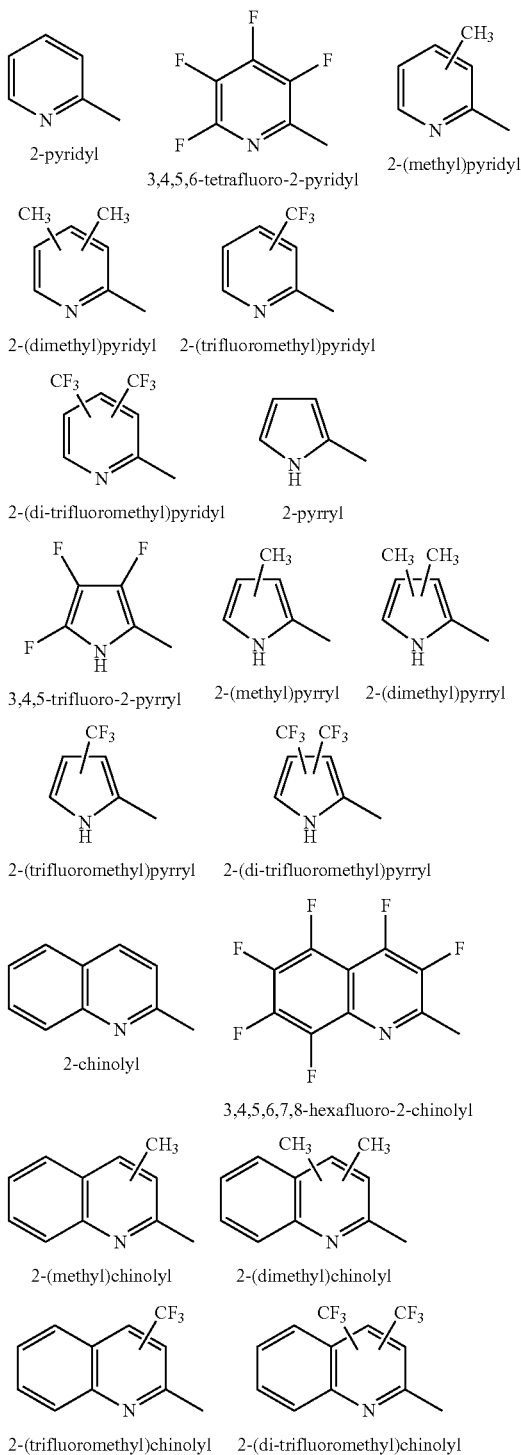

2-pyridyl   3,4,5,6-tetrafluoro-2-pyridyl   2-(methyl)pyridyl 2-(dimethyl)pyridyl   2-(trifluoromethyl)pyridyl 2-(di-trifluoromethyl)pyridyl   2-pyrryl 3,4,5-trifluoro-2-pyrryl   2-(methyl)pyrryl   2-(dimethyl)pyrryl 2-(trifluoromethyl)pyrryl   2-(di-trifluoromethyl)pyrryl 2-chinolyl 3,4,5,6,7,8-hexafluoro-2-chinolyl 2-(methyl)chinolyl   2-(dimethyl)chinolyl 2-(trifluoromethyl)chinolyl   2-(di-trifluoromethyl)chinolyl

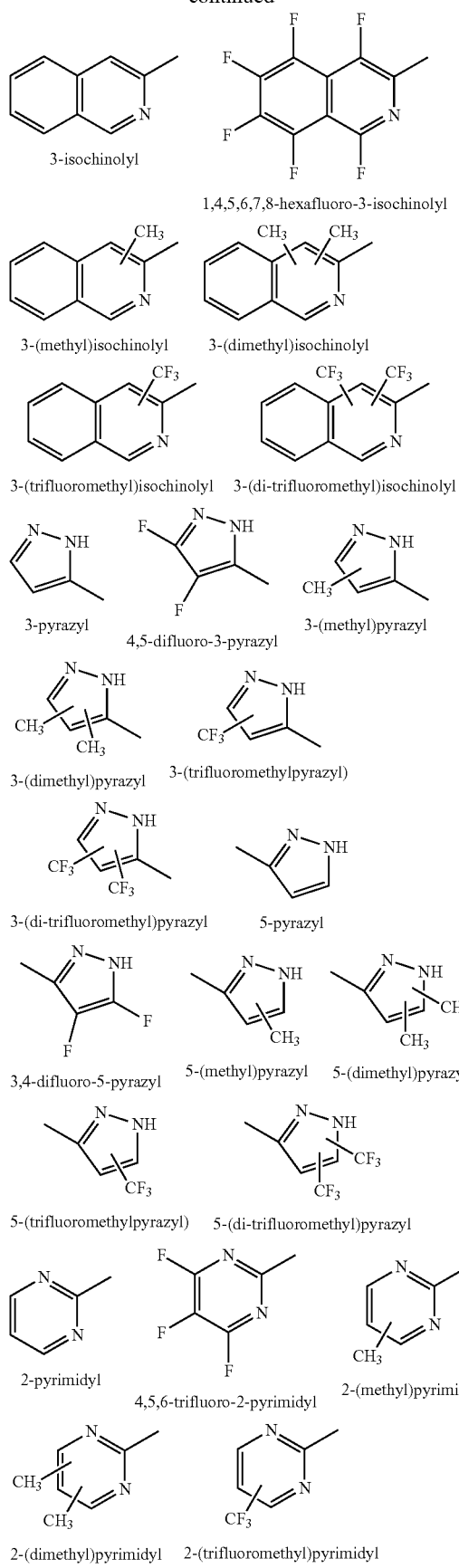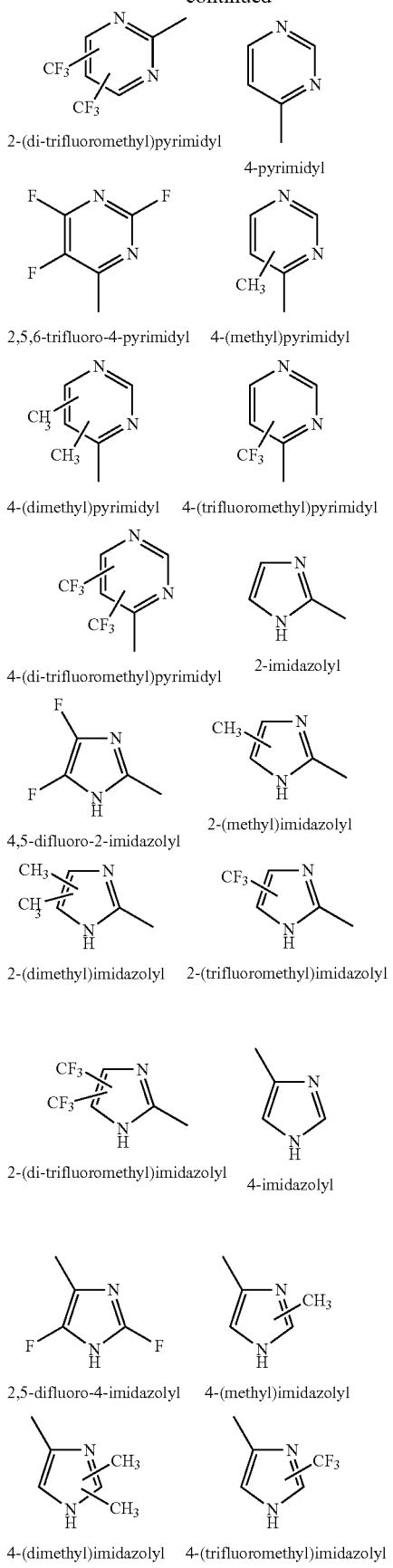

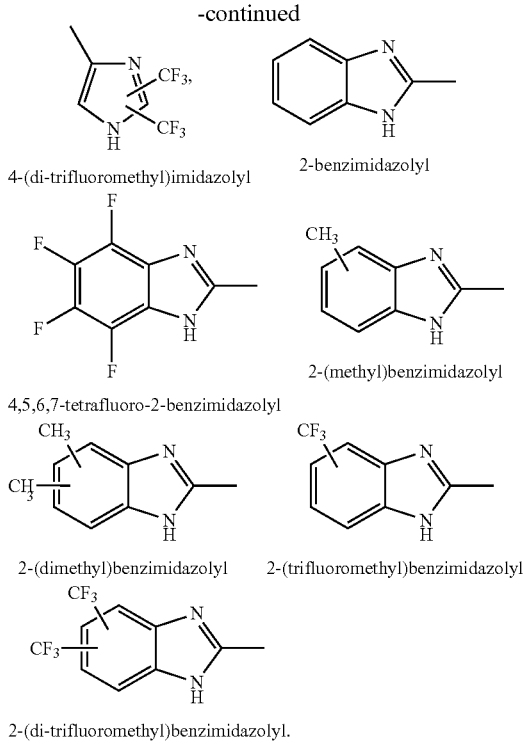

4-(di-trifluoromethyl)imidazolyl 2-benzimidazolyl 4,5,6,7-tetrafluoro-2-benzimidazolyl 2-(methyl)benzimidazolyl 2-(dimethyl)benzimidazolyl 2-(trifluoromethyl)benzimidazolyl 2-(di-trifluoromethyl)benzimidazolyl.

and wherein, in the case that one of the two groups $R_1$ or $R_2$ represents $—C(CH_3)_3$ or $—C(CF_3)_3$, the other group $R_1$ or $R_2$ is selected from $—H$, $—CH_3$ and $CF_3$.

5. Copper-(II)-oxygen adduct complexes according to claim 1, wherein
the aliphatic amine, which is bound to an alkylene group of two carbon atoms, is according to the formula

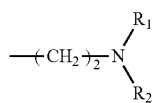

(VII)

and the nitrogen-containing heteroaromatic compound, which is bound in the 2-position to at least one of its nitrogen atoms to a methylene group, is according to the formula

(VIII)

wherein $R_1$, $R_2$ are selected from
$—H$, $—CH_3$, $—CH_2CH_3$, $—CH_2CH_2CH_3$, $—CH(CH_3)_2$, $C(CH_3)_3$,
wherein, for the case that one of the two groups $R_1$ or $R_2$ represents $—C(CH_3)_3$, the other group $R_1$ or $R_2$ is selected from $—H$ and $—CH_3$, and
Het is selected from
2-pyridyl, 2-pyrryl, 2-chinolyl, 3-isochinolyl, 3-pyrazyl, 5-pyrazyl, 2-pyrimidyl, 4-pyrimidyl, 2-imidazolyl, 4-imidazolyl, 2-benzimidazolyl.

6. Copper-(II)-oxygen adduct complexes according to claim 1, wherein the tripodal tetradentate ligand L is selected from the group tris-(2-dimethylaminoethyl)-amine, bis-[2-dimethylaminoethyl-(2-pyridylmethyl)]-amine, [(2-dimethylaminoethyl)-bis-(2-pyridylmethyl)]-amine, tris-[(2-pyridyl)-methyl]-amine.

7. Copper-(II)-oxygen adduct complexes according to claim 1, wherein $BAr_4$ stands for tetraphenylborate.

8. A method for preparing copper-(II)-oxygen adduct complexes of the general formula [L-Cu—O—O—Cu-L]$(BAr_4)_2$ according to claim 1, characterized by the steps:
a) complexing the ligand L with a Cu-(I)-compound [Cu$(R_3)_4$]X to Cu-(I)-complex [Cu-L]X in a polar aprotic solvent under inert gas atmosphere, wherein
$R_3$ represents acetonitrile or no atom and
for the case that $R_3$ represents acetonitrile, X is selected from hexafluorophosphate $PF_6^-$, tetrafluoroborate $BF_4^-$, perchlorate $ClO_4^-$, hexafluoroantimonate $SbF_6^-$, triflate $SO_3CF_3^-$, tetraphenylborate $BPh_4^-$ and tetrakis(3,5-trifluoromethyl)tetraphenylborate,
as well as in the case that $R_3$ represents no atom, X is selected from chloride $Cl^-$, bromide $Br^-$ and iodide $I^-$
b) replacement of the anion X of the Cu-(I) complex [Cu-L]X with tetraarylborate in a polar aprotic solvent under inert gas atmosphere,
c) bringing the [Cu-L]-tetraarylborate obtained after carrying out step b) into contact with an oxygen-containing atmosphere,
d) isolation and drying of the complex [L-Cu—O—O—Cu-L]$(BAr_4)_2$ obtained after carrying out step c), wherein isolation and drying occurs at deep temperatures <–70° C. and the drying occurs in the oxygen flow.

9. The method for preparing copper-(II)-oxygen adduct complexes of the general formula [L-Cu—O—O—Cu-L]$(BAr_4)_2$ according to claim 8, wherein the inert gas is selected from argon, helium, nitrogen and mixtures thereof.

10. The method for preparing copper-(II)-oxygen adduct complexes of the general formula [L-Cu—O—O—Cu-L]$(BAr_4)_2$ according to claim 8, wherein the polar aprotic solvent is selected from acetone, acetonitrile and propionitrile.

11. The method for preparing copper-(II)-oxygen adduct complexes of the general formula [L-Cu—O—O—Cu-L]$(BAr_4)_2$ according to claim 8, wherein the compound [Cu$(R_3)_4$]X used in step a) for the complexing is selected from compounds, in which $R_3$ is acetonitrile and X is selected from hexafluorophosphate $PF_6^-$, tetrafluoroborate $BF_4^-$, perchlorate $ClO_4^-$, hexafluoroantimonate $SbF_6^-$, triflate $SO_3CF_3^-$, tetraphenylborate $BPh_4^-$ and tetrakis(3,5-trifluoromethyl) tetra phenyl borate.

12. The method for preparing copper-(II)-oxygen adduct complexes of the general formula [L-Cu—O—O—Cu-L]$(BAr_4)_2$ according to claim 8, wherein the oxygen-containing atmosphere used in step c) is selected from oxygen gas, air or an oxygen-air mixture.

13. The method for preparing copper-(II)-oxygen adduct complexes of the general formula [L-Cu—O—O—Cu-L]$(BAr_4)_2$ according to claim 8, wherein
step d), i.e, the isolation and drying, is carried out before step c),
isolation and drying occur under inert gas atmosphere and wherein the isolated compound [L-Cu]$BAr_4$ is subsequently exposed according to step d) to an oxygen-containing atmosphere at room temperature as a solid.

14. The method for preparing copper-(II)-oxygen adduct complexes of the general formula [L-Cu—O—O—Cu-L]$(BAr_4)_2$ according to claim 8, wherein [Cu(CH$_3$CN)$_4$]$BAr_4$ is the compound [Cu$(R_3)_4$]X used in step a) for complexing the ligand L, and step b) is omitted.

15. In a method of using a copper-(II)-oxygen adduct complex as an oxidation catalyst, the improvement comprising using the copper-(II)-oxygen adduct complex according to claim 1 as the oxidation catalyst.

16. The method of claim 15, wherein the oxidation catalyst is used as a catalyst for the oxidation of benzene to phenol, methane to methanol, for the oxidation of hydrogen, aromatic and aliphatic, saturated and unsaturated hydrocarbons.

17. The method of claim 16, wherein the oxidation catalyst is used as a catalyst for the oxidation of benzene to phenol.

* * * * *